United States Patent
Abudula et al.

(10) Patent No.: US 11,147,901 B1
(45) Date of Patent: Oct. 19, 2021

(54) METHOD FOR REPAIRING LIVING TISSUE WITH A HOLLOW FIBER SCAFFOLD

(71) Applicant: King Abdulaziz University, Jeddah (SA)

(72) Inventors: Tuerdimaimaiti Abudula, Jeddah (SA); Usman Saeed, Jeddah (SA); Hamad Al-Turaif, Jeddah (SA); Ahmed Alshahrie, Jeddah (SA)

(73) Assignee: King Abdulaziz University, Jeddah (SA)

( * ) Notice: Subject to any disclaimer, the term of this patent is extended or adjusted under 35 U.S.C. 154(b) by 0 days.

(21) Appl. No.: 17/335,146

(22) Filed: Jun. 1, 2021

Related U.S. Application Data

(62) Division of application No. 16/848,435, filed on Apr. 14, 2020, now Pat. No. 11,103,617.

(51) Int. Cl.
    *A61L 27/26* (2006.01)
    *D01D 5/00* (2006.01)
    *C08L 1/02* (2006.01)
    *C08L 67/02* (2006.01)
    *C08L 67/04* (2006.01)

(52) U.S. Cl.
    CPC ............. *A61L 27/26* (2013.01); *C08L 1/02* (2013.01); *C08L 67/02* (2013.01); *C08L 67/04* (2013.01); *D01D 5/003* (2013.01); *D10B 2201/28* (2013.01); *D10B 2331/041* (2013.01)

(58) Field of Classification Search
    None
    See application file for complete search history.

(56) References Cited

U.S. PATENT DOCUMENTS

| | | | |
|---|---|---|---|
| 2015/0290354 A1* | 10/2015 | Loboa | D01F 1/10 424/447 |
| 2018/0002835 A1 | 1/2018 | Kumbar et al. | |
| 2018/0273746 A1 | 9/2018 | Orts et al. | |

FOREIGN PATENT DOCUMENTS

| | | |
|---|---|---|
| CN | 105780189 A | 7/2016 |
| CN | 106009538 A | 10/2016 |
| KR | 10-1791049 | 11/2017 |
| KR | 1791049 B1 | 11/2017 |
| KR | 10-1830192 | 2/2018 |

OTHER PUBLICATIONS

Abudula, et al. ; Electrospun cellulose Nano fibril reinforced PLA/PBS composite scaffold for vascular tissue engineering ; Journal of Polymer Research ; May 2019 ; Abstract Only ; 2 Pages.

Luzi, et al. ; Production and characterization of PLA_PBS biodegradable blends reinforced with cellulose nanocrystals extracted from hemp fibres ; Industrial Crops and Products, vol. 93 ; pp. 276-289 ; Dec. 25, 2016 ; Abstract Only ; 2 Pages.

* cited by examiner

*Primary Examiner* — Melissa S Mercier
(74) *Attorney, Agent, or Firm* — Oblon, McClelland, Maier & Neustadt, L.L.P.

(57) ABSTRACT

A scaffold of hollow fibers comprising a mixture of polylactic acid (PLA) and polybutylene succinate (PBS) and cellulose nanofibers (CNF), medical products made of these scaffolds and methods of using the scaffolds in regenerative medicine. A method for producing the scaffolds is also disclosed.

9 Claims, 37 Drawing Sheets

Fig. 2C                    Fig. 2D
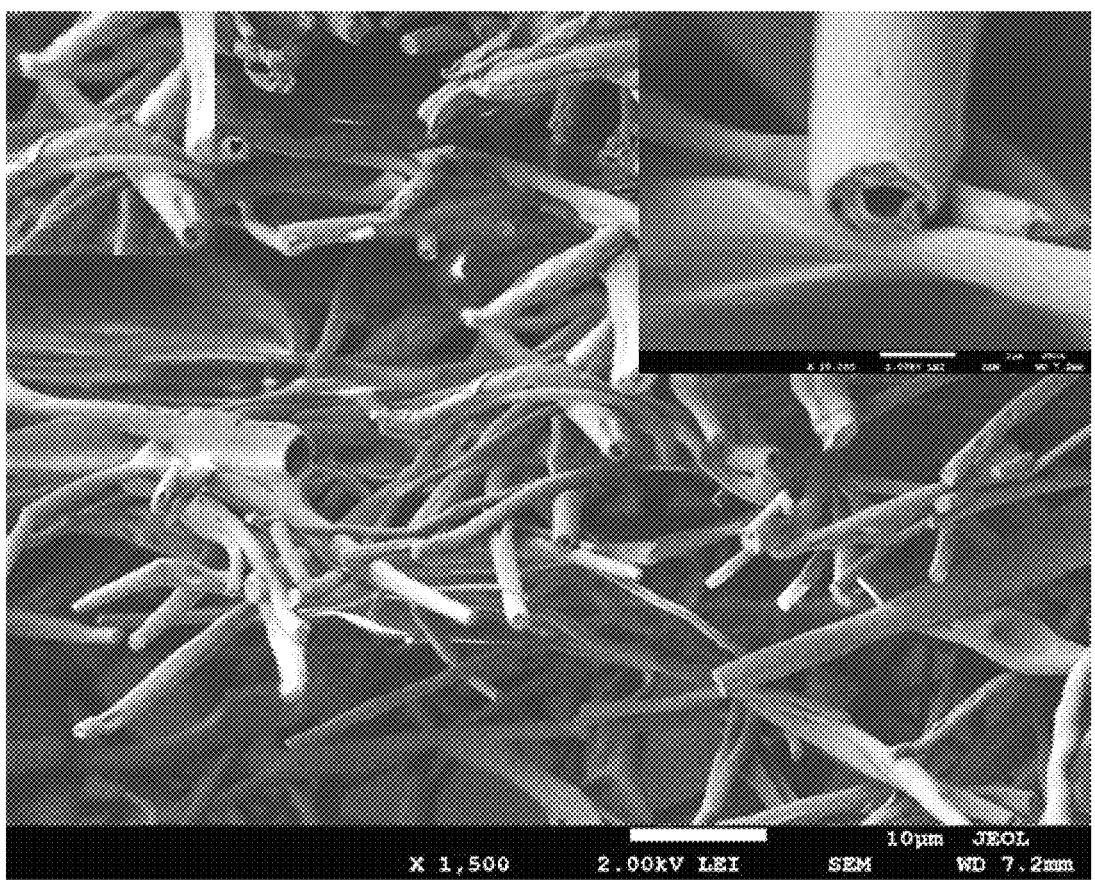

Fig. 3G                    Fig. 3H
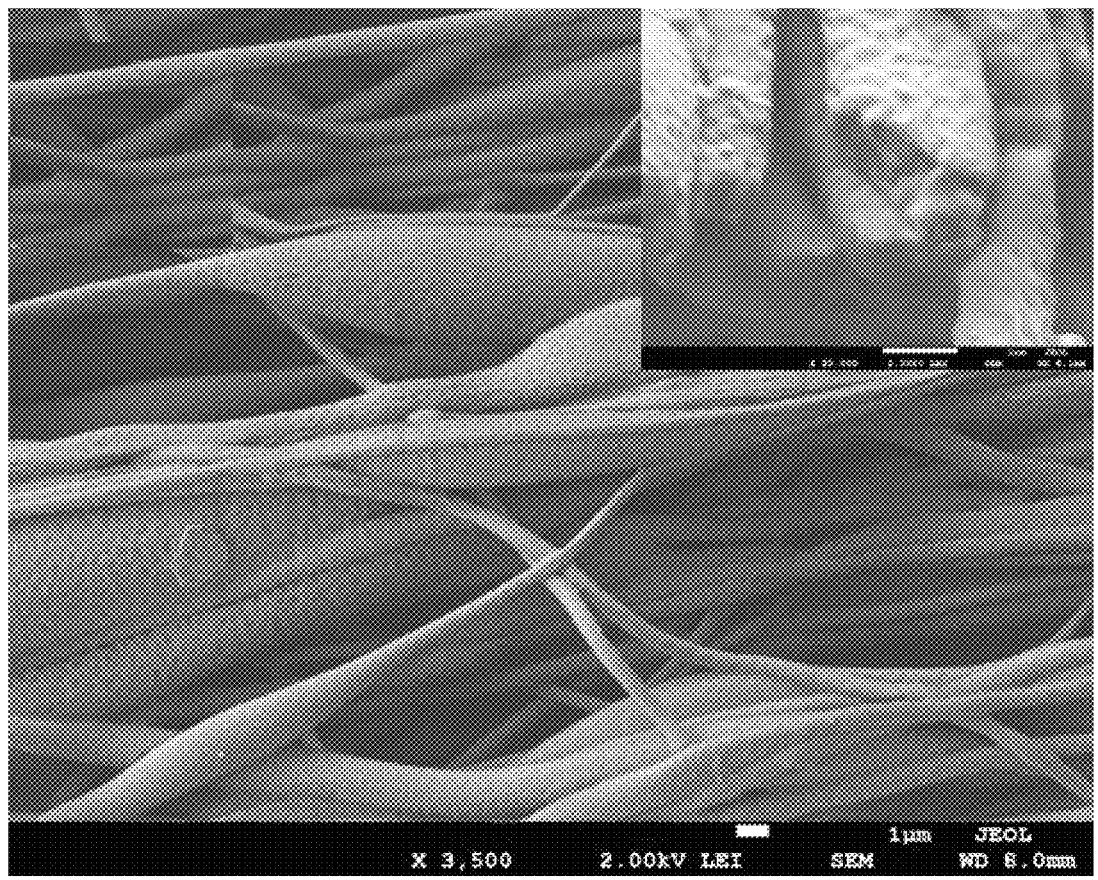

METHOD FOR REPAIRING LIVING TISSUE WITH A HOLLOW FIBER SCAFFOLD

CROSS-REFERENCE TO RELATED APPLICATIONS

The present application is a Divisional of U.S. application Ser. No. 16/848,435, now allowed, having a filing date of Apr. 14, 2020.

STATEMENT REGARDING PRIOR DISCLOSURES BY THE INVENTOR OR A JOINT INVENTOR

Aspects of this technology are described by Abudula, T., Saeed, U., Memic, A. et al. in Electrospun cellulose Nano fibril reinforced PLA/PBS composite scaffold for vascular tissue engineering. J Polym Res 26, 110 (Apr. 15, 2019) doi:10.1007/510965-019-1772-y which is incorporated herein by reference in its entirety.

BACKGROUND OF THE INVENTION

Field of the Invention

The invention pertains to the fields of tissue engineering, electrospinning, and biocompatible scaffolding.

Description of Related Art

The design and production of scaffolds for tissue engineering by electrospinning is a topic of great interest. This technology can produce scaffolds composed of micro and nano fibers from a wide variety of synthetic and natural polymers which can mimic many properties of materials found in human cells; Kishan, A. P., et al., *Recent advancements in electrospinning design for tissue engineering applications: A review*. Journal of Biomedical Materials Research Part A, 2017. 105(10): p. 2892-2905.

Electrospinning is a versatile technique which can produce materials which can mimic native extracellular matrix (ECM), such as high surface area-volume ratio, and provides a substantially interconnected porous structure; Boateng, J. S., et al., *Wound healing dressings and drug delivery systems: a review*. Journal of pharmaceutical sciences, 2008. 97(8): p. 2892-2923; Greiner, A, et al., *Electrospinning: a fascinating method for the preparation of ultrathin fibers*. Angewandte Chemie International Edition, 2007. 46(30): p. 5670-5703.Electrospun scaffolds can be designed to closely emulate both the tensile strength and elastic modulus of human tissues; Grasl, C., et al., *Electrospun polyurethane vascular grafts: in vitro mechanical behavior and endothelial adhesion molecule expression*. Journal of Biomedical Materials Research Part A: An Official Journal of the Society for Biomaterials, The Japanese Society for Biomaterials, and The Australian Society for Biomaterials and the Korean Society for Biomaterials, 2010. 93(2): p. 716-723; and Pan, Y., et al., *Small-diameter hybrid vascular grafts composed of polycaprolactone and polydioxanone fibers*. Scientific Reports, 2017. 7(1): p. 3615.

Advantageously, many antimicrobial agents, growth factors, structural materials such as proteins or carbohydrates, or anesthetic materials can be easily loaded on or into electrospun materials to fully functionalize the scaffolds for use in surgical treatments; Zhu, T., et al., *Synthesis of RGD-peptide modified polyester-urethane) urea electrospun nanofibers as a potential application for vascular tissue engineering*. Chemical Engineering Journal, 2017. 315: p. 177-190; and Wan, X., et al., *Electrospun PCL/keratin/ AuNPs mats with the catalytic generation of nitric oxide for potential of vascular tissue engineering*. Journal of Biomedical Materials Research Part A, 2018, 106(12): p. 3239-3247.

Moreover, properly designed electrospun scaffolds allow adhesion, proliferation, and migration of human cells thus facilitating regeneration of vascular tissue often with substantially recovered function in an area in need of such regeneration. Such scaffolds and methods are incorporated by reference to Khalf, A., et al., *Cellulose acetate core-shell structured electrospun fiber: fabrication and characterization*. Cellulose, 2015. 22(2): p. 1389-1400; or Du, J., et al., *Potential applications of three-dimensional structure of silk fibroin/poly(ester-urethane) urea nanofibrous scaffold in heart valve tissue engineering*. Applied Surface Science, 2018. 447: p. 269-278.

Electrospinning processes are flexible and permit many modifications including those described by and incorporated by reference to Kishan, A. P. et al., *Recent advancements in electrospinning design for tissue engineering applications: A review*. Journal of Biomedical Materials Research Part A, 2017. 105(10): p. 2892-2905 or by Phillip, M. et al., *Recent Applications of Coaxial and Emulsion Electrospinning Methods in the Field of Tissue Engineering*. BioResearch Open Access, 2016. 5(1): p. 212-227.

Among such different modifications, coaxial electrospinning received major attention in biomedical applications such as tissue engineering, wound healing and controlled drug delivery. Such modifications and methods are incorporated by reference to Kishan et al., id.; to Khodkar, F. et al., *Preparation and properties of antibacterial, biocompatible core-shell fibers produced by coaxial electrospinning*. Journal of Applied Polymer Science, 2017. 134(25); Yoon, J., et al., *Recent Progress in Coaxial Electrospinning: New Parameters, Various Structures, and Wide Applications*. Advanced Materials, 2018. 30(42): p. 1704765; and to Nguyen, T. T. T., et al., *Porous core/sheath composite nanofibers fabricated by coaxial electrospinning as a potential mat for drug release system*. International journal of pharmaceutics, 2012. 439(1-2): p. 296-306.

Despite the flexibility and other advantages of electrospinning processes, few studies report the development of a hollow fibrous structure by electrospinning due to the complexity in preparing and characterizing hollow electrospun fiber structures; Lee, G. H., et al., *Controlled wall thickness and porosity of polymeric hollow nanofibers by coaxial electrospinning*. Macromolecular Research, 2010. 18(6): p. 571-576.

This is a significant problem because hollow fibrous scaffolds are highly desirable in many tissue engineering applications. A hollow electrospun fiber can generate higher surface area and porosity compared to a solid fibrous scaffold and hollow electrospun fibers can contain pores that not only increase their surface area by which enhance permeability of, and facilitate nutrient delivery through, the hollow electrospun fibers. These properties promote and enhance uniform cellular growth and proliferation throughout and around the scaffold, as well as facilitate removal of cellular debris and byproducts of degraded scaffolds; see Yoon, J., et al., *Recent Progress in Coaxial Electrospinning: New Parameters, Various Structures, and Wide Applications*. Advanced Materials, 2018. 30(42): p. 1704765 and Tuin, et al., *Interconnected, microporous hollow fibers for tissue engineering: Commercially relevant, industry standard scale-up manufacturing*. Journal of Biomedical Materials Research Part A, 2014. 102(9): p. 3311-3323.Zhang, Y., et al., *Preparation of core-shell structured PCL-r-gelatin bi-component nanofibers by coaxial electrospinning*. Chemistry of Materials, 2004. 16(18): p. 3406-3409; Nagiah, N., et al., *Highly compliant vascular grafts with gelatin-sheathed coaxially structured nanofibers*. Langmuir, 2015. 31(47): p. 12993-13002; and Tuin, S. A., et al., *Interconnected, microporous hollow fibers for tissue engineering: Commercially relevant, industry standard scale-up manufacturing*. Journal of Biomedical Materials Research Part A, 2014. 102(9): p. 3311-3323.

In view of the limitations of existing electrospun materials, including the inability to adequately diffuse nutrients and oxygen to regenerating tissues, which often result in failure of a tissue repair to grow or regenerate, or even necrosis and cell death, the inventors sought to develop a new multifunctional material comprising a combination of polylactic acid ("PLA"), polybutylene succinate ("PBS"), and cellulose nanofibers ("CNF") that would mimic native extracellular matrix ("ECM"), serve as vascular prostheses, and/or exhibit other advantageous properties such as acting as an artificial vascular system delivering nutrients to regenerating tissue thus enhancing tissue regeneration.

SUMMARY OF THE INVENTION

The foregoing paragraphs have been provided by way of general introduction, and are not intended to limit the scope of the following claims. The described embodiments, together with further advantages, will be best understood by reference to the following detailed description taken in conjunction with the accompanying drawings.

Among its other aspects, the invention is directed to a CNF reinforced, homogenously blended, microporous hollow fibrous PLA/PBS scaffold suitable and to methods of using this scaffold for tissue regeneration and for vascular tissue engineering.

Another aspect of the invention is directed to a method for coaxial electrospinning to produce these hollow fibrous composite scaffolds having the physical and functional properties disclosed herein.

Embodiments of the invention include, but are not limited to the following.

One aspect of the invention is directed to a homogenous scaffold comprising, consisting essentially of, or consisting of fibers having a hollow core and a peripheral shell, wherein the peripheral shell comprises polylactic acid (PLA), polybutylene succinate (PBS) and cellulose nanofibers (CNF). Homogenous mixing of the PLA, PBS and CNF within the nanofibers of the scaffold in different volumes or segments of the fiber different in composition by no more than 0.1, 0.2, 2.5, 0.5, 1, 2, 5 or 10% determined by X-ray photoelectron spectrometry ("XPS"). A maximum weight percentage of CNF in a PLA/PBS matrix is 2.5% which defines the coherency in the shell polymer.

In an alternative embodiment, the scaffold may comprise solid fibers of PLA and PBS containing CNF in the same amounts disclosed herein for the corresponding hollow fibers.

In another alternative embodiment, the scaffold may comprise hollow or solid fibers of 60 to 40 wt. % PLA and 40 to 60 wt. % PBS without CNF. Such fibers are produced by electrospinning without a core material such as glycerol or mineral oil. In one embodiment the feed rate for a stock solution comprising PLA and PBS into an electrospinning device may range from 0.2, 0.5, 1.0, 1.5 to 2.0 mL/hr.

Typically the peripheral shell of the hollow fibers comprises 40, 45, 50, 55 to 60 wt. % PLA and 60, 55, 45, or 40 wt. % of a mixture of PBS and CNF, based on a total weight of the PLA, PBS and CNF in the peripheral shell. The mixture of PBS and CNF typically contains 1, 2, 3, 4 to 5 wt. % CNF based on the combined weight of the PBS and CNF. Shell stock solutions may contain higher concentrations of CNF depending on the amount of solvent so as to provide a final CNF concentration in the peripheral shell between about 1 and 5 wt. %.

In one embodiment, peripheral shell of the hollow fibers comprise a mixture of about 50 wt. % PLA and about 50 wt. % of a mixture of PBS and CNF, based on a total weight of the PLA, PBS and CNF, wherein said mixture of PBS and CNF contains 1, 2 or 3 wt. % CNF, preferably about 2 wt. % CNF based on the combined weight of the PBS and CNF.

The hollow fibers of the scaffold may have average diameters ranging from 400, 500, 600, 700, 800, 900 to 1,000 nm and the hollow core has a diameter ranging from 300, 400, 500, 600, 700, 800 to 900 nm. In one embodiment the fibers have an average diameter ranging from 500, 600, 700 to 800 nm and the hollow core has a diameter ranging from 400, 500, 600 to 700 nm. A preferred diameter of the shell ranges from 600 to 1000 nm and a preferred diameter of the hollow core diameter ranges from 200 to 500 nm. The range of diameter typically depends on the feed rate of the shell and core solution.

The peripheral shell of the fibers of the scaffold may comprise uniformly distributed pores ranging from about 25, 30, 35, 40, 45, 50, 55, 60, 65, 70, 75, 80, 85, 90, 95 to 100 nm in diameter. The hollowness of the fibers and/or their porosity permits nutrient solutions, such as cell culture medium, or other soluble agents to permeate through the fibers.

In one embodiment the diameter of the hollow fibers ranges from about 580, 600, 620, 640, 660, 680, 700, 720 to about 730 nm; the core shell thickness of the fibers ranges from about 290, 300, 320, 340, 360, to about 365 nm and the core shell comprises uniformly distributed pores about 40, 45, 50, 55 to about 60 nm in diameter and has a wettability characterized by a water contact angle of less than about 35, 40, 45, 50, 55, or 60 degrees. In a related embodiment, these hollow fibers are produced by, and have the features derived from, electrospinning a core material comprising glycerol at a core feed rate of about 0.07, 0.08 or 0.09 mL/hr and a shell stock solution comprising PLA, PBS and CNF at a shell feed rate of about 0.9, 1.0 to 1.1 mL/hr.

Another embodiment is directed to a scaffold comprising hollow fibers having average diameters ranging from about 600, 650, 700 to about 750 nm, a core shell thickness ranging from to about 310, 320, 340, 360, 380 to about 400 mm wherein said core shell comprises uniformly distributed pores about 35, 45, 50, 55 to about 60 nm in diameter, and a water contact angle of less than 40, 45, 50, 55 or 60 degrees. In a related embodiment, these hollow fibers are produced by, and have the features derived from, electrospinning a core material comprising mineral oil at a core feed rate of about 0.09, 0.1 to 0.11 mL/hr and a shell stock solution comprising PLA, PBS and CNF at a shell feed rate of about 0.9, 1.0 to 1.1 mL/hr.

A related embodiment is directed to a composition comprising the scaffolds as disclosed herein. Such compositions include a sterile or aseptic patch, packing, dressing or bandage comprising the scaffold or mesh as disclosed herein and, optionally, may be coated with or otherwise contain cells or one or more biologically active agents or structural materials. In some embodiments the scaffolds may be preseeded with stem cells or other partially or fully differentiated cells, including autologous, allogenic, or xenogeneic cells or harvested native cells or cultured cells including but not limited to cultured stem cells. Alternatively a scaffold may be exposed to regenerative cells once placed in situ so that cells attach or move into the scaffold. Such cells may migrated from adjacent bodily tissues or blood or be injected. Such cells may be alive and capable of division or rendered incapable of division by exposure to a chemical or radiological agent. In some embodiments such cells will embryonic stem cells, bone marrow stem cells (BMSCs), or mesenchymal stem cells (MSCs) or other cells capable of regenerating damaged tissue.

A scaffold may also be coated or otherwise contacted with a biologically active agent such as or more hemostatic agents, cytokines, growth factors, desiccants, vitamins, antimicrobial agents, analgesics, anti-inflammatory agents, or combinations thereof. Other coatings include structural materials such as proteins like fibrin or collagen or other components of the ECM.

Another aspect of the invention is directed to a method for repairing, regenerating or otherwise healing or growing a tissue comprising applying the scaffold as disclosed herein on, in or around a tissue in need of repair. Any tissue may benefit for use of the scaffold as disclosed herein, especially vascularized tissues in need of a ready supply of oxygen and other nutrients delivery of which can be enhanced via a scaffold. In some embodiments a scaffold may be surgically implanted or imposed on a target tissue or organ and in others it may be injected or inserted laparoscopically.

In some embodiments, the scaffold may be preseeded with stem cells or cells similar or identical to the tissue or organ in need of regeneration. In other embodiments a scaffold once in place may become populated with cells that migrate into it or otherwise attach to it and help heal or regenerate a target tissue.

The tissue in need of repair may be a vascularized tissue containing arteries, veins, capillaries or lymphatic vessels. Highly vascularized tissues include muscle tissue, lung tissue and liver tissue. The scaffold as disclosed herein may be used to vascular or endovascular tissues such as those forming the arteries, veins, capillaries and heart tissues. It may be used to heal or regenerate tissues of the heart, kidney, liver, spleen, pancreas, bladder, skeletal muscle, small bowel, large bowel, stomach, bone, brain, or lung.

The scaffold may be used in reconstructive surgery or treatment of acute or chronic wounds or in orthopedic surgeries such as those involving spine diseases, sports injuries, degenerative diseases, infections, tumors, and congenital disorders. It may be used to treat skin or other tissue that has been wounded, punctured, lacerated, crushed, burned or otherwise damaged. It may be used to treat surgical wounds including those resulting from plastic surgery. It may be used during treatment of bone fractures or correction of bone defects or other surgeries involving bone. It may be used to facilitate healing or regeneration of the jaw or teeth.

In another embodiment, the scaffold as disclosed herein may be used to treat or enhance healing or regeneration of a poorly vascularized or avascular tissues such dense connective tissue or cartilage.

In some embodiments, the scaffold may be used to regenerate or grow a tissue ex vivo or in vitro for study or for reimplantation.

Another embodiment of the invention involves a method for producing a scaffold, of hollow fibers comprising co-axially electrospinning fibers which contain a core and a peripheral shell; wherein the core comprises glycerol, mineral oil or another immiscible (with the shell solution) fluid, and the shell comprises a mixture of polylactic acid (PLA), polybutylene succinate (PBS) and cellulose nanofibers (CNF); and removing the glycerol or mineral oil from the core and volatiles from the shell.

In some embodiments of this method the co-axial electrospinning comprises feeding glycerol or mineral oil (or another liquid immiscible with a shell forming solution) to an inner layer of a co-axial spinneret at a core feed rate ranging from about 0.05, 0.06, 0.07, 0.08, 0.09 to 0.1 mL/hr and feeding a shell forming solution comprising PLA, PBS and CNF into an outer layer of the spinneret at a shell feed rate ranging from 0.5 to 2.0 mL/hr. In some embodiments of this method the core feed rate is 0.08, 0.09, 0.10, 0.11, to 0.12 mL/hr and the shell feed rate is 0.8, 0.9, 1.0, 1.1 to 1.2 mL/hr.

During electrospinning the resulting fibers are stretched. Typically, the fibers are stretched over a distance of 6, 8, 10, 12, 14, 16, to 18 cm at a voltage ranging from 15, 20 to 25 kV.

In one embodiment the shell forming solution comprises shell components in an amount ranging 40, 45, 50, 55 to 60 wt. % PLA and 60, 55, 50, 45 to 40 wt. % of a mixture of PBS and CNF, based on a total weight of the PLA, PBS and CNF; wherein said mixture of PBS and CNF contains 1, 2, 3, 4 to 5 wt. % CNF based on the combined weight of the PBS and CNF; and wherein said solution comprises at least one organic solvent dissolving the shell components. In one embodiment the shell-forming solution comprises about 40, 50 or 60 wt. % of the shell components (PLA and PBS/CNF), preferably about 50 wt. %, and wherein the at least one organic solvent dissolving the shell components is a mixture of chloroform and ethanol at a volumetric ratio of 2:1, 3:1, or 4:1 preferably about 3:1.

BRIEF DESCRIPTION OF THE DRAWINGS

A more complete appreciation of the invention and many of the attendant advantages thereof will be readily obtained as the same becomes better understood by reference to the following detailed description when considered in connection with the accompanying drawings, wherein:

FIGS. 2C-2D. Cross-section by SEM of hollow fibrous scaffolds made of glycerol at a 1 ml/h shell feed rate and at a 0.05 ml/hr core feed rate.

FIGS. 3G-3H. Cross-section by SEM of hollow fibrous scaffolds made of mineral oil at a 1 ml/h shell feed rate and at a 0.15 ml/hr core feed rate.

DETAILED DESCRIPTION OF THE INVENTION

The inventors recognized the significant disadvantages of using solid fibrous scaffolds for tissue engineering as these induce the formation of necrotic cores within a scaffold designed to induce recovery or regeneration in large tissue defects. This is because the boundary of the scaffold is often blocked by seeded cells, hence vital nutrients cannot be transported properly to cells in the central area of the scaffolds.

In contrast, the microporous walls and hollowness in the hollow fiber scaffolds disclosed herein provide external channels for mass transport to ensure the cellular growth throughout the scaffold. Therefore, the cell viability, growth rate and tissue recovery rate are greatly enhanced.

Surprisingly, compared to corresponding solid fiber scaffolds, the formation of hollow fiber scaffolds showed a significant decrease in the contact angle and wettability. In terms of contact angle and wettability, as shown herein, the morphological structure of the PLA/PBS/CNF hollow fiber scaffolds was determined to be more significant than their composition. It was found that both PLA and PBS exhibit hydrophobic surface properties, but their 50/50 wt. % combination reduced the water contact angle by more than 30°. Surprising it was also found that the incorporation of CNF into the PLA/PBS fiber also reduced the water contact angle; compare 50/50 with C4 in FIG. 8.

Figure 9:
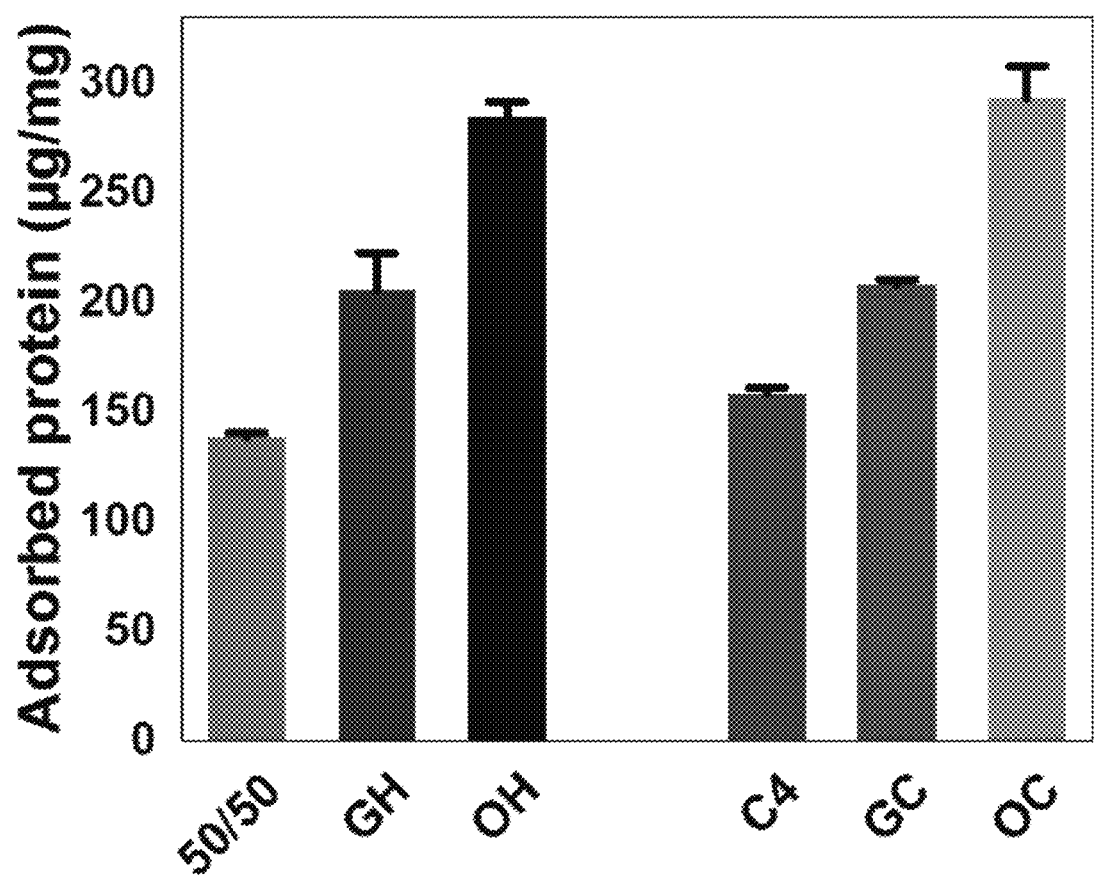
FIG. 9. Protein adsorption capacities of hollow fibrous scaffolds (GH, OH, GC, OC) compared to the solid fibrous scaffolds (50/50, C4). The Y-axis unit is "adsorbed protein in μg/mg and shows the amount of protein adsorbed in each mg of scaffold.
Figure 10A:
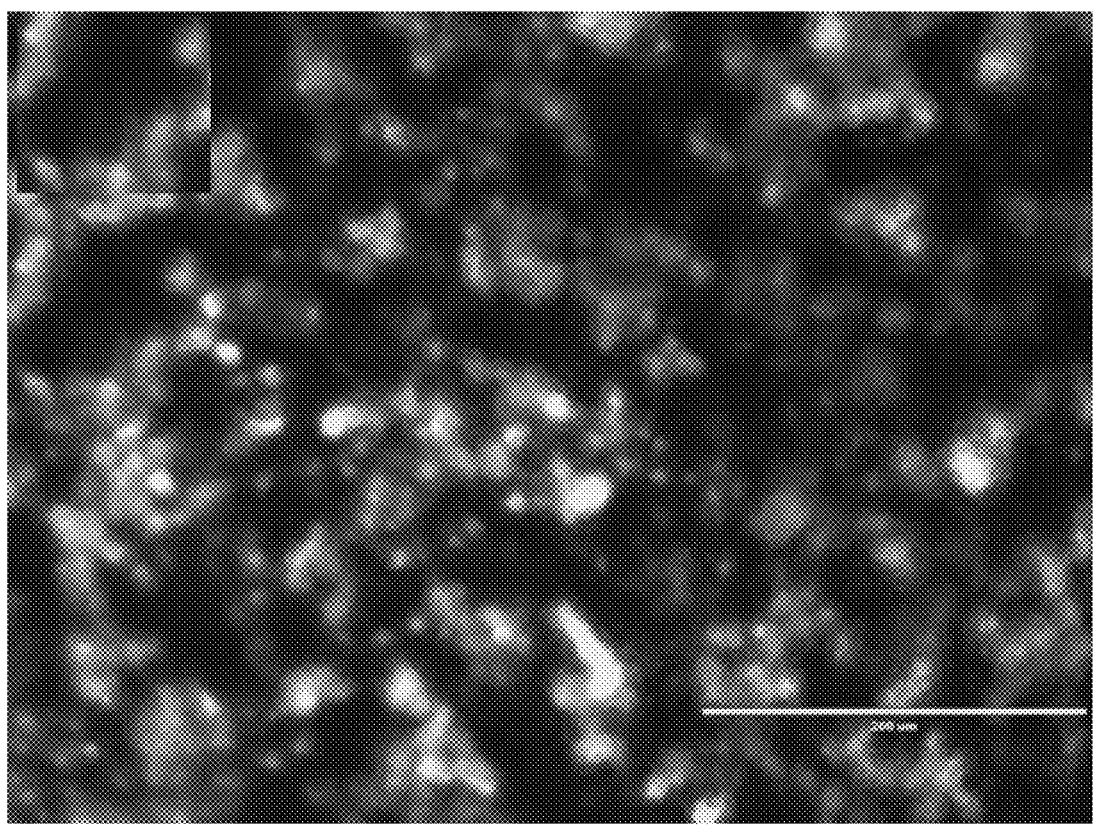
FIGS. 10A-10D. GFP/DAPI stained images of GH (FIG. 10A), OH (FIG. 10B), GC (FIG. 10C) and OC (FIG. 10D) hollow fibrous scaffolds after 7 days of cell culturing.
Figure 10B:
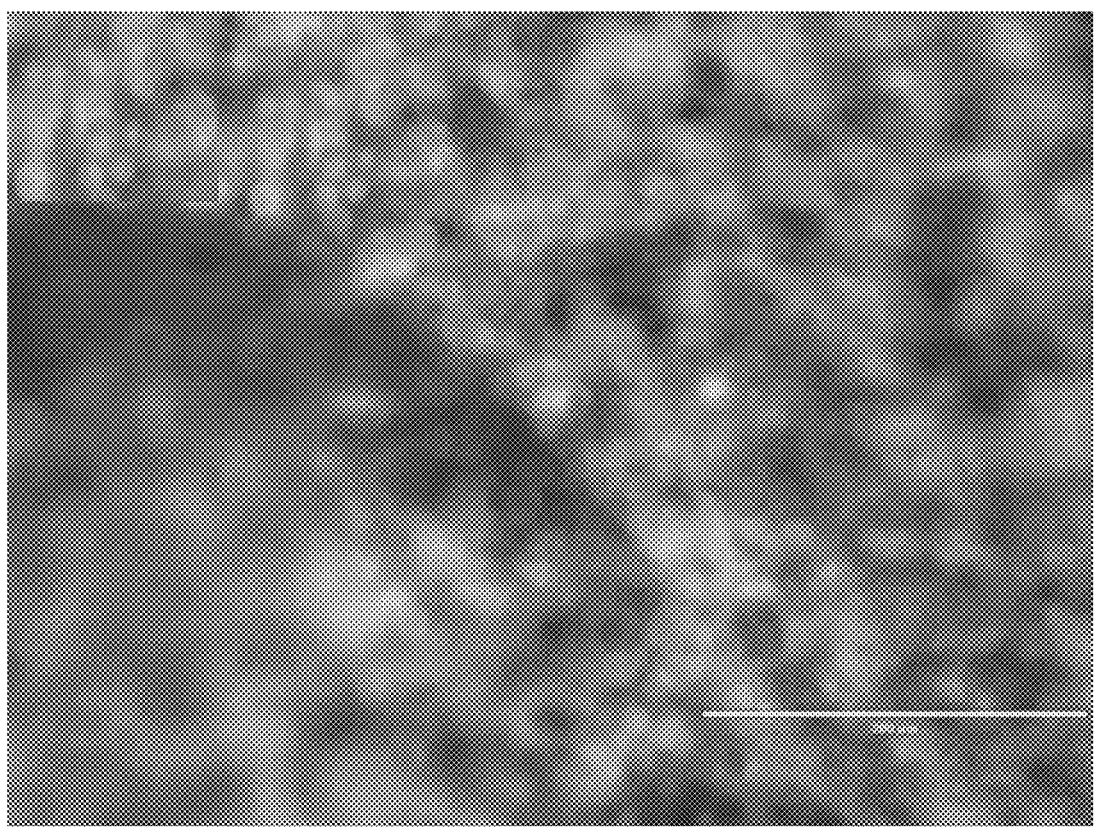
Figure 10C:
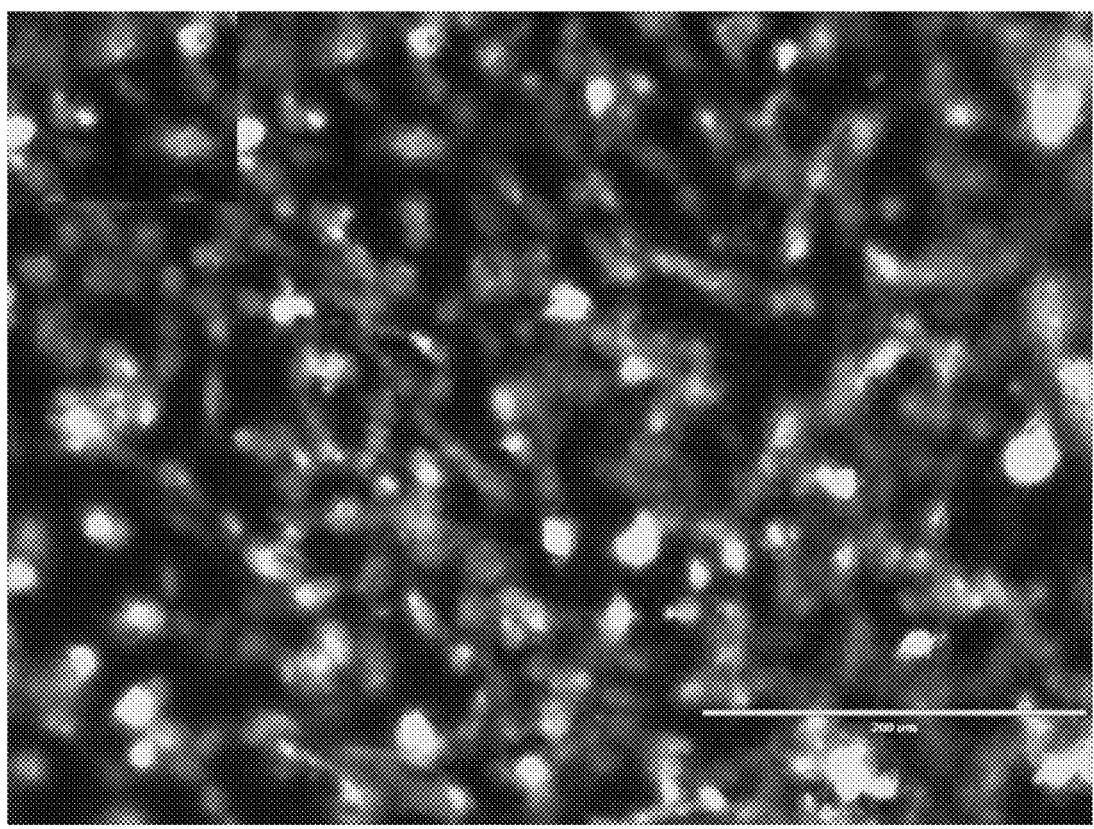
Figure 10D:
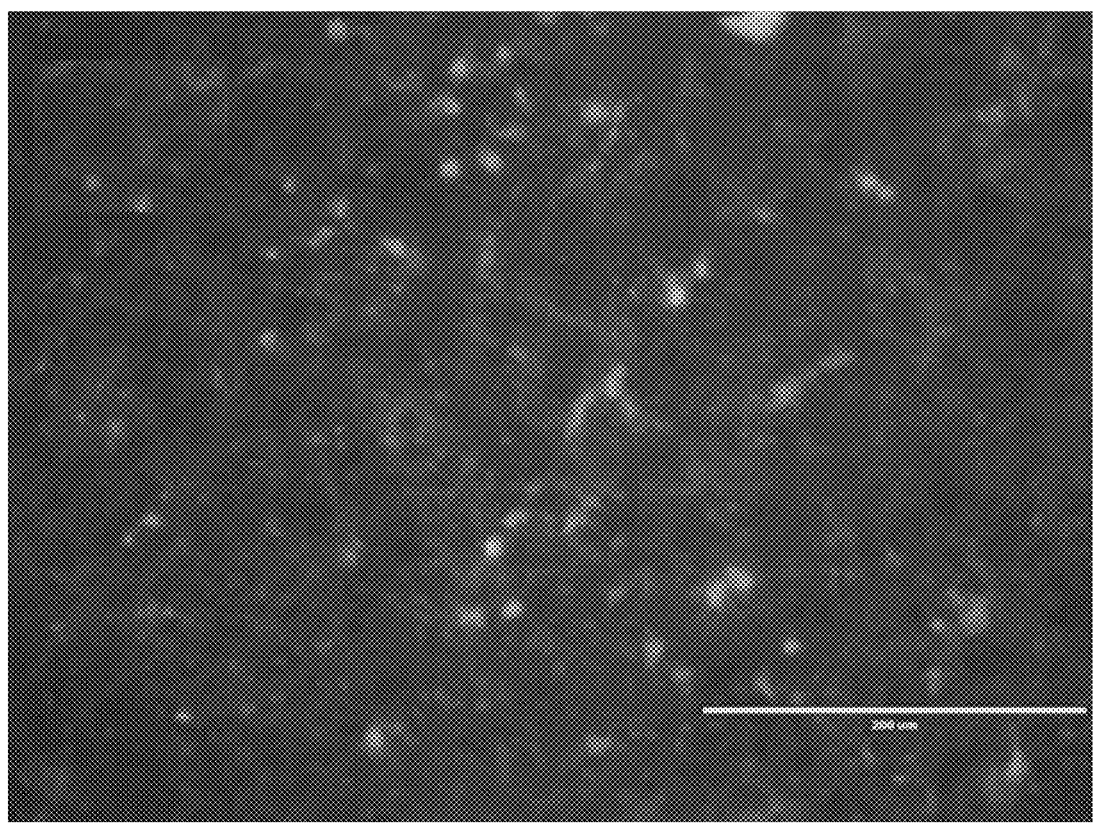

Furthermore, protein adsorption results in FIG. 9 showed that the large surface area, which resulted from the use of microporous hollow fibrous scaffold, attracted more protein to the scaffold surface and that the incorporation of hydrophilic nano cellulose fibrils (CNF) further enhanced protein adsorption. Enhancement of protein adsorption to a scaffold can provide a microenvironment for sufficient cell-cell interaction, cell migration, proliferation and differentiation required for tissue repair or regeneration.

Surprisingly, mechanical testing results showed that strength, elasticity and hardness of the hollow fibrous scaffolds were not significantly different than those of the solid fibrous scaffold.

The flexibility and ductility of the hollow fibrous scaffolds was much lower when compared to a stiffer solid fibrous scaffold. This may be due to an increase in the number of interfaces in the hollow fibrous scaffolds which can act as crack initiation or stress concentration sites. The incorporation of cellulose nanofibrils into hollow fibers not only significantly increased the strength and elastic modulus of the scaffold but also improved the flexibility. In contrast for the solid fiber, ductility and flexibility of the scaffold were not significantly affected by the presence of cellulose nanofibrils.

Polylactic acid ("PLA"), an aliphatic polyester, is a widely studied synthetic polymer for use in tissue engineering due to its renewability, biodegradability and cost effectiveness; O'Brien, F. J., *Biomaterials & scaffolds for tissue engineering*. Materials today, 2011. 14(3): p. 88-95; Gigli, M., et al., *Poly (butylene succinate)-based polyesters for biomedical applications: A review*. European Polymer Journal, 2016. 75: p. 431-460; and Hardiansyah, A., et al., *Electrospinning and antibacterial activity of chitosan-blended poly(lactic acid) nanofibers*. Journal of Polymer Research, 2015. 24(4): p. 59m each incorporated herein by reference in their entirety.

Polybutylene succinate ("PBS") is an aliphatic polyester polybutylene that is flexible, has a high degree of crystallinity, biodegradable, and has cell-friendly surface characteristics. The inventors have recognized that PBS, as a relatively soft polymer compared to PLA, can provide a plasticizing effect on the mechanically stiff but brittle PLA.

As disclosed herein, it is possible to reinforce a PLA/PBS matrix using cellulose nanofibrils (CNF) which can be synthesized from the most abundantly found natural polymer cellulose; Benitez, A. and A. Walther, *Cellulose nanofibril nanopapers and bioinspired nanocomposites: a review to understand the mechanical property space*. Journal of Materials Chemistry A, 2017. 5(31): p. 16003-16024; and Hanif, Z., et al., *Butanol-mediated oven-drying of nanocellulose with enhanced dehydration rate and aqueous re-dispersion*. Journal of Polymer Research, 2017. 25(3): p. 191, each incorporated herein by reference in their entirety.

In some embodiments, the cellulose nanofibrils or CNF will have lengths ranging from 1, 2, 3, or >3 μm, diameters ranging from <0.5, 0.5, 1, 2, 3, 4, 5, 6, 7, 8, 9, 10, 11, 12, 13, 14, 15, 20 or 30 nm as measured by TEM.

In some embodiments, the ratio of length to diameter of a CNF may range from 200:1, 150:1 to 100:1. In some embodiments, CNF can exhibit a mechanical performance characterized by an elastic modulus in the range of 40-50 GPa, preferably about 46.6 GPa and a tensile strength in the range of 1000 to 1200 MPa, preferably about 1170 MPA. Physical properties of CNF are incorporated by reference to Clemons, C., *Nanocellulose in spun continuous fibers: A review and future outlook*. Journal of Renewable Materials, 2016. 4(5): p. 327-339. Typically, the CNF are ultrathin nanofibrils with large length to width aspect ratio. The average width of CNF is 50±10 nm and length is 2000±240 nm resulting in an aspect ratio of L/w=40±4. The average ratio of diameter to length is 0.025±0.002. During the electrospinning process single CNFs were uniformly dispersed into PLA/PBS matrix without agglomeration. The phenomenon can be identified from atomic force microscopy (AFM) images; see FIGS. 12A and 12B.

The nanoscale characteristics of CNF are helpful in achieving high magnitude of orientation and high moisture adsorption capacity which are favorable for medical applications. Moreover, it is advantageous compared to other reinforcing agents such as carbon nanotube in terms of biocompatibility and bioactivity.

Figure 12A:
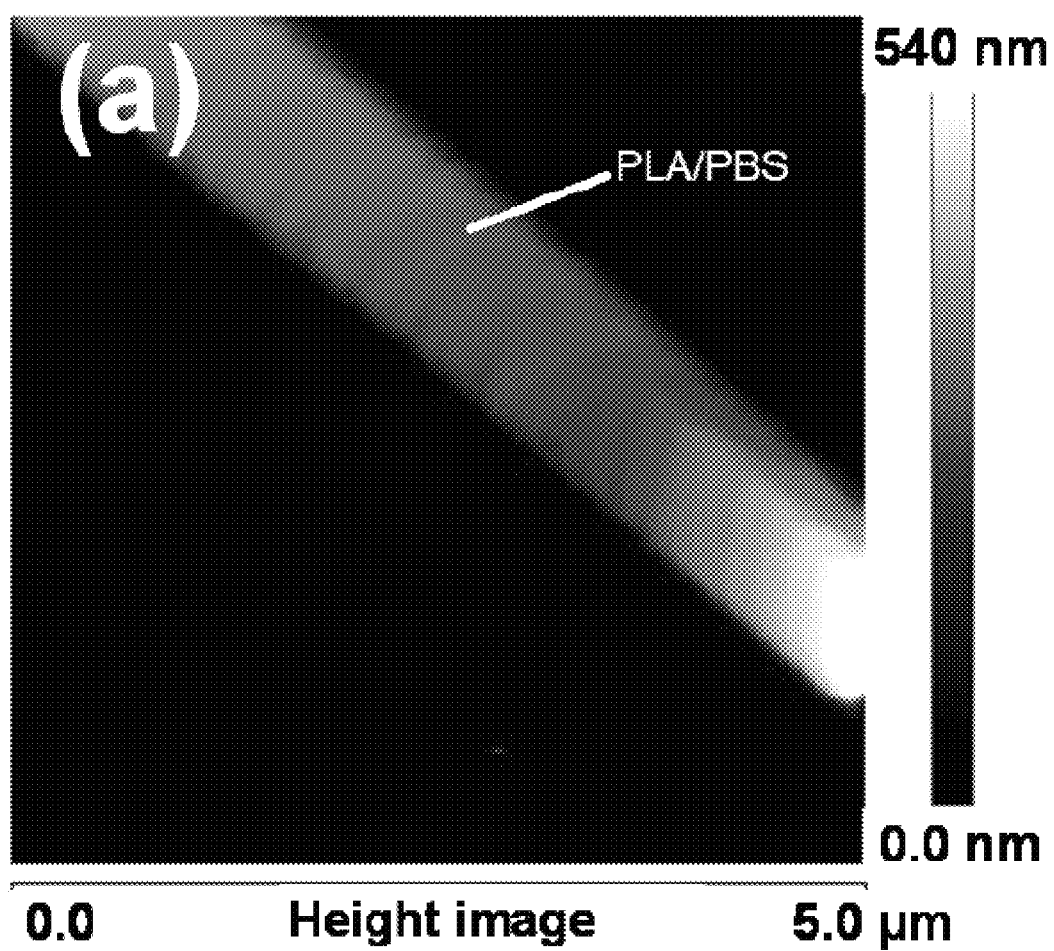
FIG. 12A. AFM surface topography of electrospun PLA/PBS single fiber.
Figure 12B:
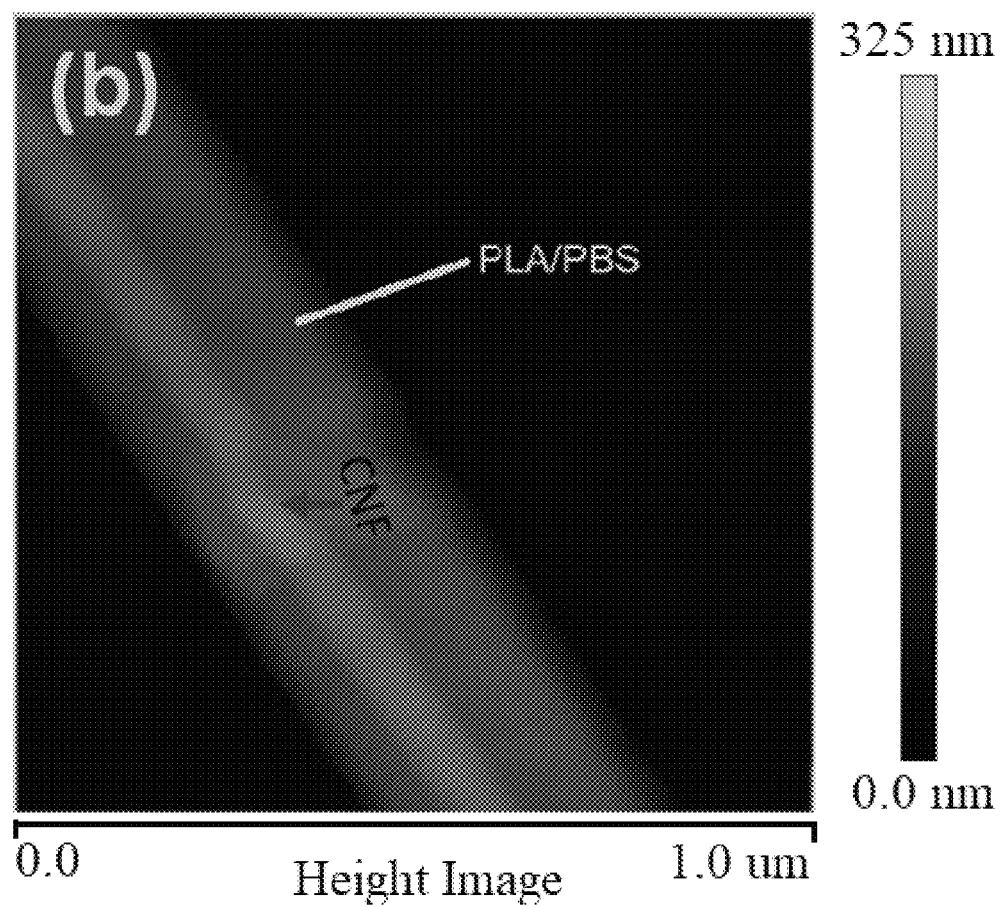
FIG. 12B. AFM surface topography of electrospun PLA/PBS/CNF composite single fiber.

An AFM analysis was performed on the CNF incorporated PLA/PBS and noticed that CNF is not only conjugated into the PLA/PBS matrix but also CNF orientation is exactly parallel to the electrospun fiber; see FIGS. 12A and 12B. This implies that the orientation of CNF can be tailored by electrical charge during the process of electrospinning.

The moisture adsorption capacity of CNF ranges from about 13 to 24 g water/g CNF. A 3-(4,5-dimethylthiazol-2-yl)-2,5-diphenyl tetrazolium bromide (MTT) assay test was performed on the electrospun scaffolds. The CNF contained scaffolds supported cell attachment and growth without showing any adverse effects. The cell growth rate on the CNF reinforced composite was much better than for the control reference. These results show that the CNF is 100% biocompatible making its suitable for biomedical applications.

In view of these advantageous properties, it is not necessary to incorporate other types of fibers, fillers or particles non-CNF forms of cellulose, such as cellulose nanoballs or nanopellets, sisal or hemp fibers, or shorter cellulose nanowhiskers, cellulose nanocrystals, cellulose nanorods, which have needle-like or rod-like morphologies and have shorter length to diameter ratios than CNF; or other organic or inorganic fillers such as silver or other metals, or clays into the fibers as disclosed herein.

Porosity. Scaffolds per se or the walls of the scaffold fibers may contain pores, preferably uniformly distributed pores where the number of pores in different areas of the fiber vary by no more than 5, 10, 15, or 20%. In most embodiments, the sizes of the pores in the walls of the scaffold fibers will be no more than 20, 30, 40, 50, 60, 70, 80, 90 or 100 nm, preferably from about 40 to about 60 nm.

In some embodiments, the scaffolds may contain pores ranging from >100, 200, 500 to 1,000 nm, or in scaffolds, at least 1, 2, 5 or 10 µm. Preferably, the pores in the scaffold are uniformly sized and distributed, for example, where the average size or numbers of pores in different areas of the scaffold or scaffold fiber walls differ by no more than 1, 2, 5, 10, or 20% in average area or average number. Apart from the porosity of the fiber walls, the scaffold itself has a porosity ranging from about 3, 4, 5, 6, 7, 8, 9, to 10 µm. The developed scaffold is an interconnected macroporous structure having average pore size of about 3.5 µm.

Wettability of the scaffold or its fibers can be determined by measurement of the water contact angle. In some embodiments, the water contact angle of a scaffold as disclosed herein, ranges from not more than 10, 25, 30, 35, 40, 45, to 50° or any intermediate value within this range. Typically, the water contact angle of a scaffold of hollow fibers as disclosed herein will be less than that of a scaffold of compositionally similar solid, non-hollow fibers. As disclosed herein the inventors have also found that a combination of PLA and PBS (e.g. about a 40/60, 50/50 or 60/40 wt. % combination) reduces the water contact angle of the hollow fibers, for example by at least 10, 20, or 30 degrees when compared to a solid fiber A scaffold or mesh, such as a scaffold used for tissue engineering, is a structure made of artificial or natural substances that acts as a shape on which cells can grow. A scaffold can be inert and not interact with the cells growing on it, or it can actively help the cells to grow by releasing chemical signals and/or nutrients. A scaffold can be partially or completely biodegradable or non-biodegradable. Typically a scaffold as disclosed herein comprises hollow fibers made of PLA, PBS and CNF, is wettable, and has a surface roughness and porosity that permits it to bind to proteins and cells. The hollowness and porosity of the fibers permits enhanced transport of nutrients to cells growing on the scaffold. These features permit it to provide a suitable biocompatible microenvironment for the sufficient cell-cell interaction, cell migration, proliferation and differentiation. In preferred embodiments the scaffold as disclosed herein is biodegradable.

The thickness of a flat scaffold or conformation of a shaped scaffold may be selected based on the type of tissue being repaired or regenerated. In some embodiments, the thickness of a scaffold as disclosed herein will range from <0.1, 0.1, 0.2. 0.5, 1, 2, 5, 10 or >10 mm. Preferably, a flat sheet scaffold has a thickness of 0.05, 0.1, 0.2, 0.5, 1.0 to 2 mm which is mainly dependent on electrospinning time.

In some embodiments, the scaffold may be coated with or otherwise incorporate one or more therapeutic, prophylactic, or diagnostic agents, such as hemostatic agents, anti-infectives, growth factors, cytokines, stem cells, cultured cells such as induced stem cells, or other cells such as autologous or allogenic cells, anesthetics, vasoconstrictors, ECM components such as collagen (including Types 1, 2, 3, 4 and 5), fibrin, chitosan, glycosaminoglycan including hyaluronic acid, laminin, or fibronectin, antibodies or complement factors. These additional components may be coated or attached on the surfaces of, or in the hollow cores of, electrospun fibers.

Electrospinning procedures. Electrospinning uses an electrical charge to draw very fine (typically on the micro or nanoscale) fibers from a liquid. One skilled in the art may select a commercially available electrospinning device equipped to feed the core and shell solutions into the inner and outer layers of spinnerets sized to produce the hollow fibers as disclosed herein. Core-shell fibers may be produced by using a co-axial nozzle for electrospinning as described by and incorporated by reference to Yarin A L, et al.. Evolution of core-shell structure: From emulsions to ultra-fine emulsion electrospun fibers. J. Mater. Chem. 2007; 17: 2585. The co-axial nozzle comprises two cylinders with one cylinder situated within the core of a larger bore cylinder. Two different solutions are dispensed simultaneously through the inner and outer cylinders and charged in the same way as conventional single bore nozzle. There are several parameters that can be modified to control the size of the fibers and the volume ratio of the core and shell material.

Fiber diameter can be controlled by the nozzle diameter while the volume ratio is by the feed-rate of the core and shell solution as described by and incorporated by reference to Chakraborty S, et al., *Electrohydrodynamics: A facile technique to fabricate drug delivery systems.* Adv Drug Deliv Rev 2009; 61: 1043. Those skilled in the art may select an appropriate electrospinning device, for example, from those which are commercially available. Such devices are available, and incorporated by reference to, the Electrospinning Device Catalogue hypertext transfer protocol://electrospintech.com/espincatalogue.html#.Xg4B de-WzIU (last accessed Jan. 2, 2020).

Electrospinning stock solutions used to make the hollow fibers as disclosed herein typically comprise, for the core feed, glycerol, mineral oil, or another solvent that is immiscible with the stock solution for the shell. However, glycerol and mineral oil may be slightly soluble in some shell stock or precursor solutions as long as the degree of solubility does not significantly affect electrospinning of the core and shell.

As shown herein electrospinning is a versatile technique to produce fibrous scaffold which mimics the native extracellular matrix (ECM) for vascular prosthesis because conventional solid fibrous scaffolds lack the ability of nutrient diffusion and have poor permeability resulting in the cell death and tissue necrosis. A hollow fibrous scaffold can greatly improve permeability and nutrient diffusion throughout the scaffold. The hollow fibers have vessel-like micro or nano structures which can serve as an excellent artificial vascular system.

The inventors have developed scaffolds of hollow fibers comprising a unique combination of cellulose nanofibrils (CNF) reinforcing a PLA/PBS composite which are produced by a coaxial electrospinning technique forming a homogenous blended and hollow microporous fibrous structure. Glycerol and mineral oil were used as core templates which were removed by evaporation. Both templates allowed hollow fiber formation and uniform pore dispersion in the walls of the hollow fibers occurred when the mineral oil was used. The scaffold made by mineral oil template showed an enhanced wettability and protein adsorption capacity which may be due to the pore size distribution in the hollow fibers. These hollow fibrous scaffolds demonstrated superior ability to permit cell attachment and cellular proliferation as shown by a cell culture test and should provide a more favorable microenvironment for regeneration of tissues, such as to regenerate healthy vascular tissue.

Example

Materials. Polylactic acid (PLA 2003D) was purchased from Nature Works, USA. Poly butylene succinate (PBS, commercial name is Bionolle) was obtained from Showa Denko, Japan. Cellulose Nanofibrils (CNF) was acquired from University of Maine, USA. Dulbecco's Modified Eagle's Medium (DMEM) was purchased from Lonza, USA. Proteinase K solution (20 mg/ml), Dulbecco's phosphate-buffered saline and 10% fetal bovine serum (FBS) was purchased from Thermo Fisher Scientific Inc., Fair Lawn, N.J. Glycerol was obtained from Loba Chemie Pvt Ltd, India. Mineral oil (P3) is from Pfeiffer Vacuum, Germany. Chloroform, ethanol, sodium dodecyl sulfate (SDS), Lysozyme, tris buffer solution (0.1 M, pH-7), calcium chloride ($CaCl_2$) and sodium azide ($NaN_3$) were from Sigma-Aldrich, St. Louis, Mo., USA.

Preparation of hollow fibrous scaffold. A mixture of PLA and PBS at a weight ratio of 50/50 was dissolved in chloroform and ethanol with 3:1 volume ratio by stirring for 3 hours.

In order to incorporate CNF into PLA/PBS, CNF/PBS composites with 4% of CNF concentrations were prepared first by melt extrusion. Then, the mixture of PLA and CNF/PBS composite in equal weight ratio was dissolved in the same solvent system overnight.

A Nanon 101A electrospinning setup (NANON Supply, MECC, Fukuoka, Japan) was adapted for Coaxial Electrospinning. An ultra-thin coaxial spinneret (NANON Supply, MECC, Fukuoka, Japan) was used to create coaxial electrospun fibers. The PLA/PBS solution or the composite solution was delivered to outer layer of the spinneret by a system provided with a syringe pump using a Teflon® (Polytetrafluoroethylene)tube at 1 mL/h of feed rate.

An extensional syringe pump (KDS 100, KD Scientific Inc., USA) connected with Teflon® tube was used to deliver the core materials into a 27-gauge blunt metallic needle.

The double layer solution was electrically stretched at 20 kV of voltage over 12 cm of distance and finally collected on flat aluminum sheet.

Two types of materials were selected for the core layers which were glycerol and mineral oil. Initial adjustments were performed on both materials using PLA/PBS solution as a shell layer.

After electrospinning, the collected samples were placed in oven at 55° C. to evaporate the core solution. It was found that full evaporation of glycerol can be achieved in 24 hours while 5~6 days were needed to evaporate the mineral oil from the sample. The prepared samples were named according to their core-shell composition before drying, as shown in Table 1.

TABLE 1

Abbreviated name of hollow fiber, according to their core-shell composition

| Scaffold Name | Core material | Core feed rate (mL/h) | Shell material | Shell feed rate (mL/h) |
| --- | --- | --- | --- | --- |
| GH | Glycerol | 0.08 | PLA/PBS | 1.0 |
| GC | Glycerol | 0.08 | PLA/PBS/CNF | 1.0 |
| OH | Mineral oil | 0.1 | PLA/PBS | 1.0 |
| OC | Mineral oil | 0.1 | PLA/PBS/CNF | 1.0 |
| 50/50 (solid) | — | — | PLA/PBS | 0.5 |
| C4 (solid) | — | — | PLA/PBS/CNF | 0.5 |

Characterization. The morphological features of the prepared fibers were observed using a Field emission scanning electron microscopy (FESEM, JEOL JSM 7600F, Tokyo, Japan). A customized image processing method was employed to calculate size distribution of the fibers. The SEM images were processed through adjustment, Gaussian smoothing, local thresholding and noise removal. Additionally, the fiber sizes were calculated by Canny Edge based Euclidian distance transform.

The cross-section of the hollow fibrous scaffold was evaluated using SEM to confirm fiber hollowness and measure the inner diameter. The scaffold was frozen in liquid nitrogen and cut with a razor blade. The core removal was performed after cutting the sample and mounting it on the SEM specimen in order to avoid any deformation of the fiber cross section.

The XPS measurements for the prepared scaffolds were carried out in an ultra-high vacuum multi-technique surface analysis system (SPECS GmbH, Germany). A standard dual anode X-ray source SPECS XR-50 with Mg-Kα, 1283.6 eV was used to irradiate the sample surface. The power of X-ray on the sample surface was 100 W and a take-off-angle for electrons relative to sample surface plane was 90°. The pressure in the analysis chamber was kept at $5\times10^{-9}$ bar during the measurements. The wide scan survey spectra and high energy resolution narrow scan spectra were recorded at room temperature.

A 180° hemispherical energy analyzer model PHOIBOS-150 and a set of nine channel electron multipliers MCD-9 was adopted for scanning. The analyzer was operated in Fixed Analyzer Transmission (FAT) and medium area lens modes at pass energy of 30 eV, step size of 1.0 eV for survey scans. The pass energy was set at 20 eV with step size of 0.025 eV and dwell times of 0.1 sec for narrow or high resolution scans.

As the standard practice in XPS studies, the hydrocarbon $C^{1s}$ line (284.6 eV) corresponding to C—C bond has been used as binding energy reference for charge correction. The high energy resolution spectra were obtained under analysis conditions that would give a FWHM=0.85 eV from the Ag $3d_{5/2}$ signal of freshly argon ion etched silver (Ag) sample.

The surface wettability of the fibrous mat was analyzed according to water contact angle measurement performed by drop shape analyzer (DSA 100). The BCCM was composed of 90% Dulbecco's Modified Eagle's Medium (DMEM) and 10% fetal bovine serum ("FBS"). A 2 ul of liquid was slowly dropped on the surface of the fiber mash then contact angle was determined as an angle between the drop contour and the projection of the surface (baseline).

The protein attachment test was performed by the fibrous mats which were cleaned by DPBS (Dulbecco's phosphate-buffered saline). The fibrous mats were placed in 10% of FBS in DMEM for 24 hours. The samples were washed again by DPBS to remove unattached proteins. The mats were placed after washing in 2% of SDS (sodium dodecyl sulfate) for 3 hours to release the attached proteins. The protein concentration was measured according to the UV adsorption using the Nanodrop 2000. Also, the calculation was based on UV absorbance at 280 nm wavelength, where BSA (Bovine Serum Albumin) was used as reference.

Biocompatibility test. The scaffolds collected on circular glass cover slips (diameter 124 mm) by two hours of electrospinning, were initially sterilized under UV for 1 h followed by PBS washes (thrice for 5 min each). The scaffolds were then washed with 100% ethanol for 10 min and again washed thrice with phosphate buffered saline. The scaffolds were then primed in the culture media and incubated at 37° C. incubator in a 5% $CO_2$ in air atmosphere for 24 h to ensure no contamination. The scaffold thickness was about 0.2 mm. A preferred range for scaffold thickness is about 0.05 to 2 mm depending on the particular vascular tissue engineering application such as prosthesis of aorta, arteries and other smaller blood vessels.

Subsequently, the media was removed and fresh medium containing dermal fibroblasts ($2\times10^4$ cells/well) of a 24 well tissue culture plate was added to the four different scaffolds and cultured at standard culture conditions of 37° C. in a 5% $CO_2$ incubator with regular changes of media every 48 h.

After culturing for 7 days, the scaffolds were stained using cell tracker fluorescent probe (CMFDA, c7025) to visualize the cell attachment on to the scaffolds. A fluorescent dye (5 µM) was added to cells in fresh media and incubated for 30 min under standard culture conditions. The media containing the dye was then removed and the scaffolds containing the cells washed once with PBS to remove any traces of the unbound dye and then the cell were fixed in 70% ice-cold ethanol for 10 min. After phosphate buffered saline washes the cells were incubated with 4'-6-Diamidino-2-phenylindole (DAPI) and green florescence protein (GFP) for 5 min at room temperature and washed with phosphate buffered saline again. The cells were then studied using fluorescent microscope (EVOS® FL Imaging System, Thermo Fisher Scientific).

The cell proliferation assay was performed using an MTT reagent kit (3-(4,5-dimethylthiazolyl-2)-2,5-diphenyltetrazolium bromide; Sigma). The 10 mL MTT reagent (final concentration of 0.5 mg/mL) was added to the medium in the culture dishes and the dishes were incubated for 4 h until a purple precipitate was visible. The medium was then removed and 100 mL of the detergent reagent was added into the dishes and incubation carried out in the dark for 2 h. The absorbance at 570 nm was spectrophotometrically measured using a microplate reader (SpectraMax i3, San Jose, USA) with a reference wavelength of 570 nm.

Figure 1:
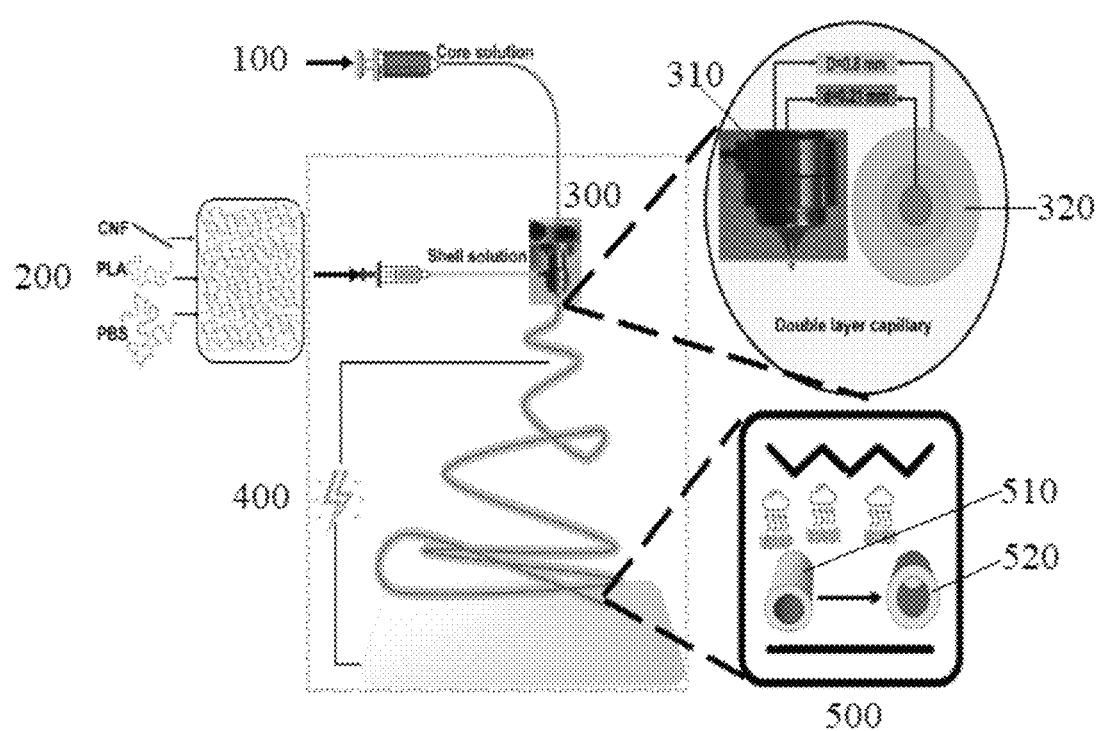
FIG. 1 schematically illustrates one embodiment of hollow fiber preparation and design based on a coaxial electrospinning method. Core solution 100 and shell solution 200 are fed to a spinneret 300 which comprises a spinneret fitting 310 and a double layer capillary 320, electric force 400 draws the materials out of the spinerette and produces a core-filled filament 510. The core is removed by evaporation step/evaporator 500 forming a hollow fiber 520.
Figures 2A, 2B:
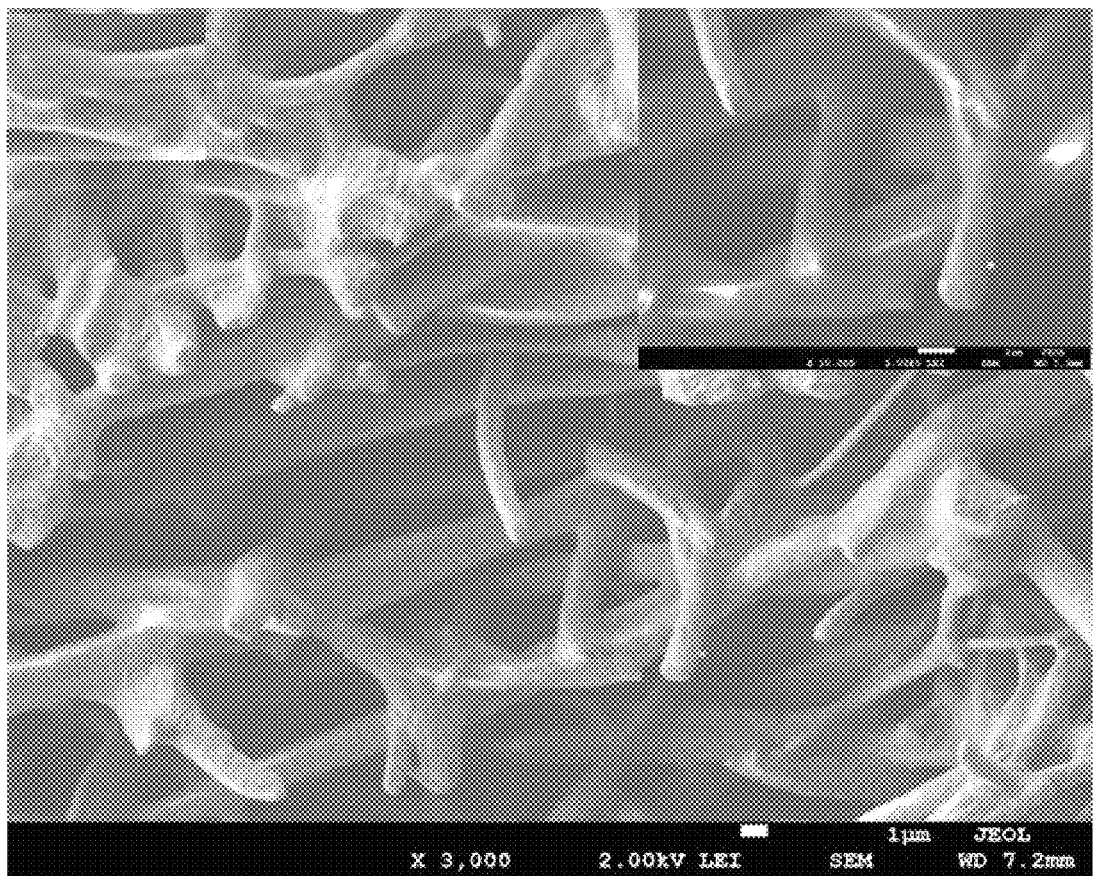
FIGS. 2A-2B. Cross-section by SEM of hollow fibrous scaffolds made of glycerol at a 1 ml/h shell feed rate and at a 0.03 ml/hr core feed rate.
Figures 2E, 2F:
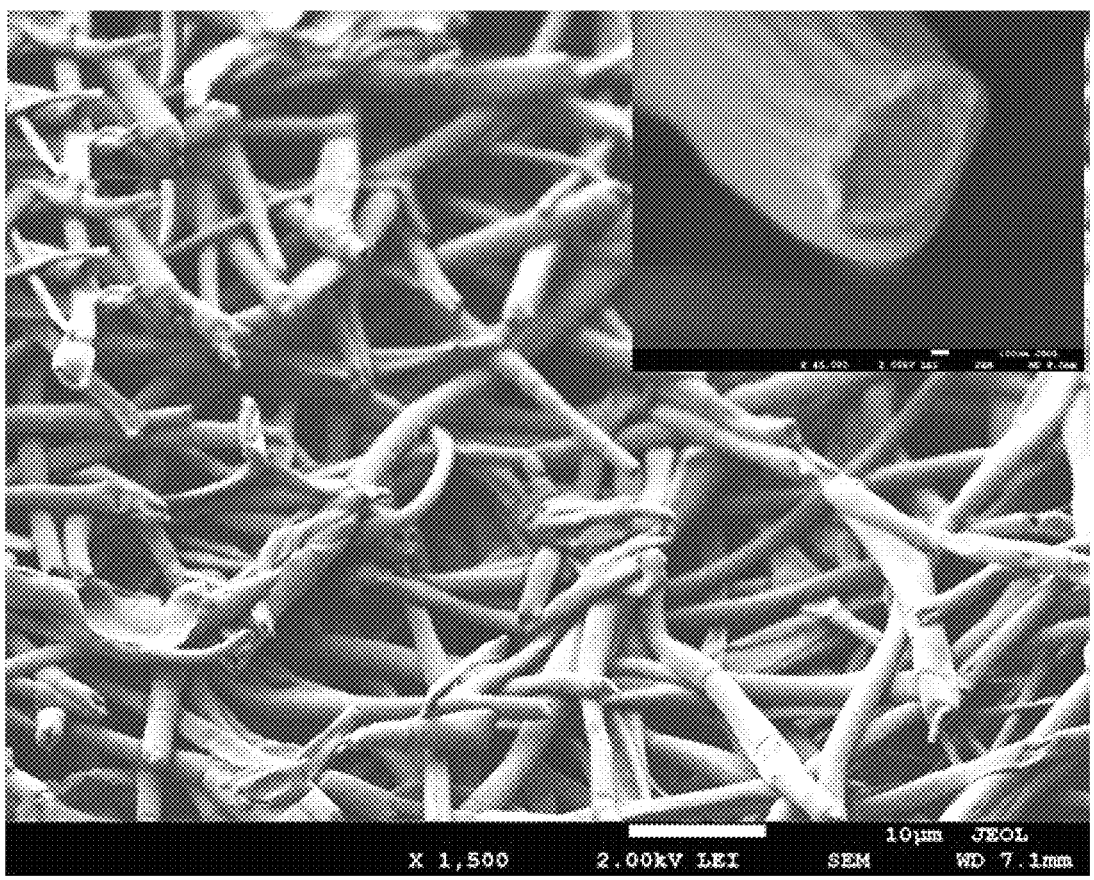
FIGS. 2E-2F. Cross-section by SEM of hollow fibrous scaffolds made of glycerol at a 1 ml/h shell feed rate and at a 0.08 ml/hr core feed rate.
Figures 2G, 2H:
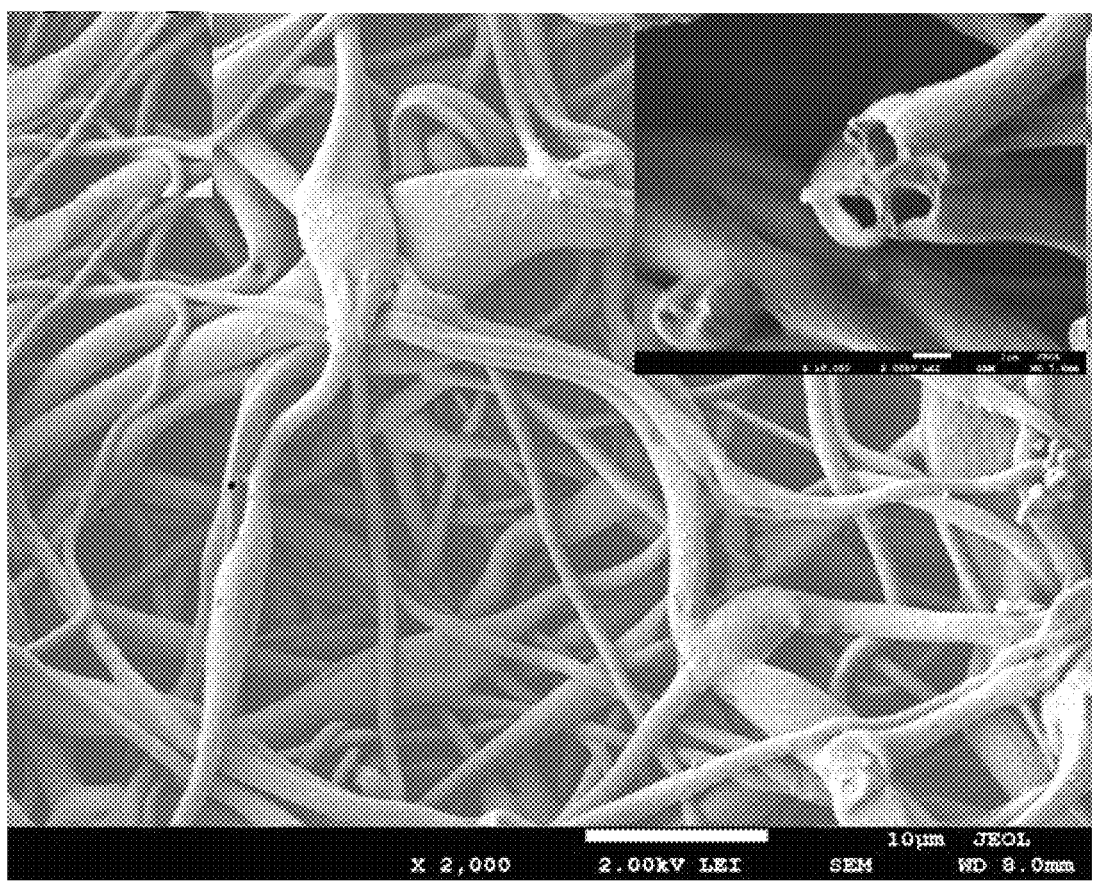
FIGS. 2G-2H. Cross-section by SEM of hollow fibrous scaffolds made of glycerol at a 1 ml/h shell feed rate and at a 0.10 ml/hr core feed rate.
Figures 2I, 2J:
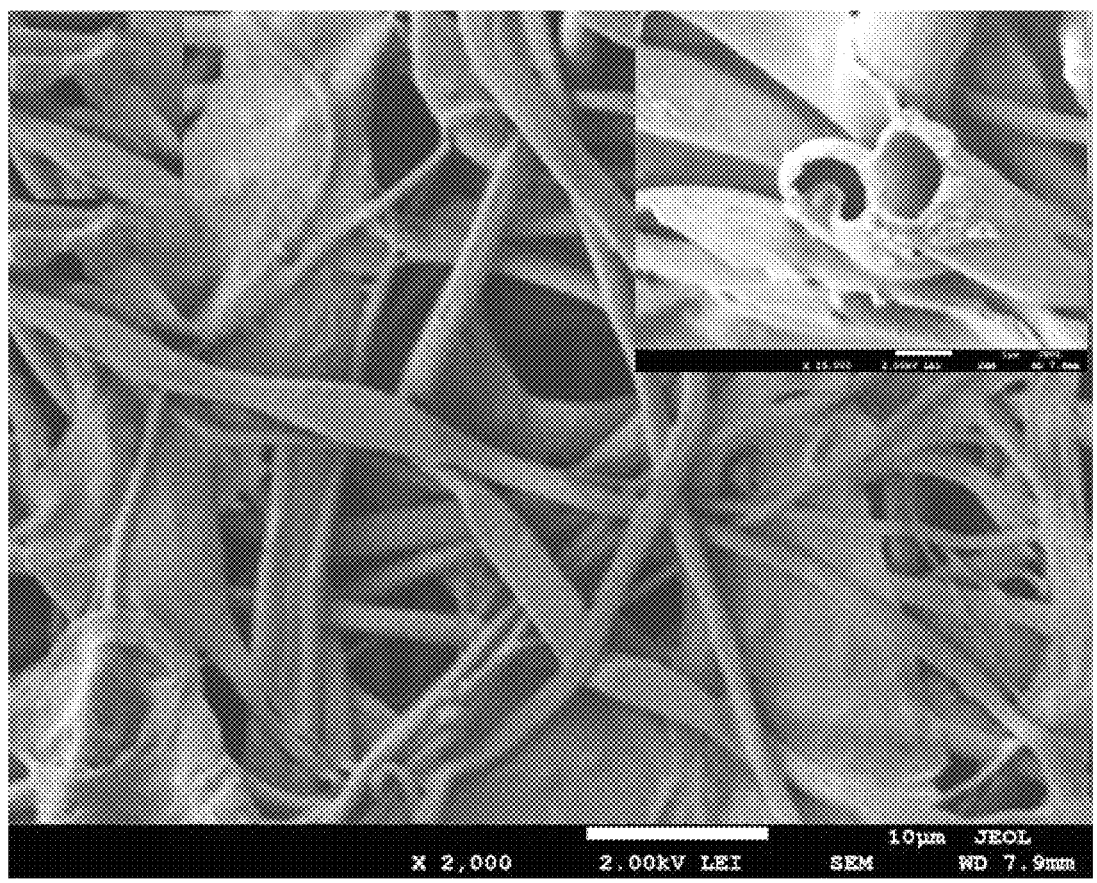
FIGS. 2I-2J. Cross-section by SEM of hollow fibrous scaffolds made of glycerol at a 1 ml/h shell feed rate and at a 0.12 ml/hr core feed rate.
Figures 2K, 2L:
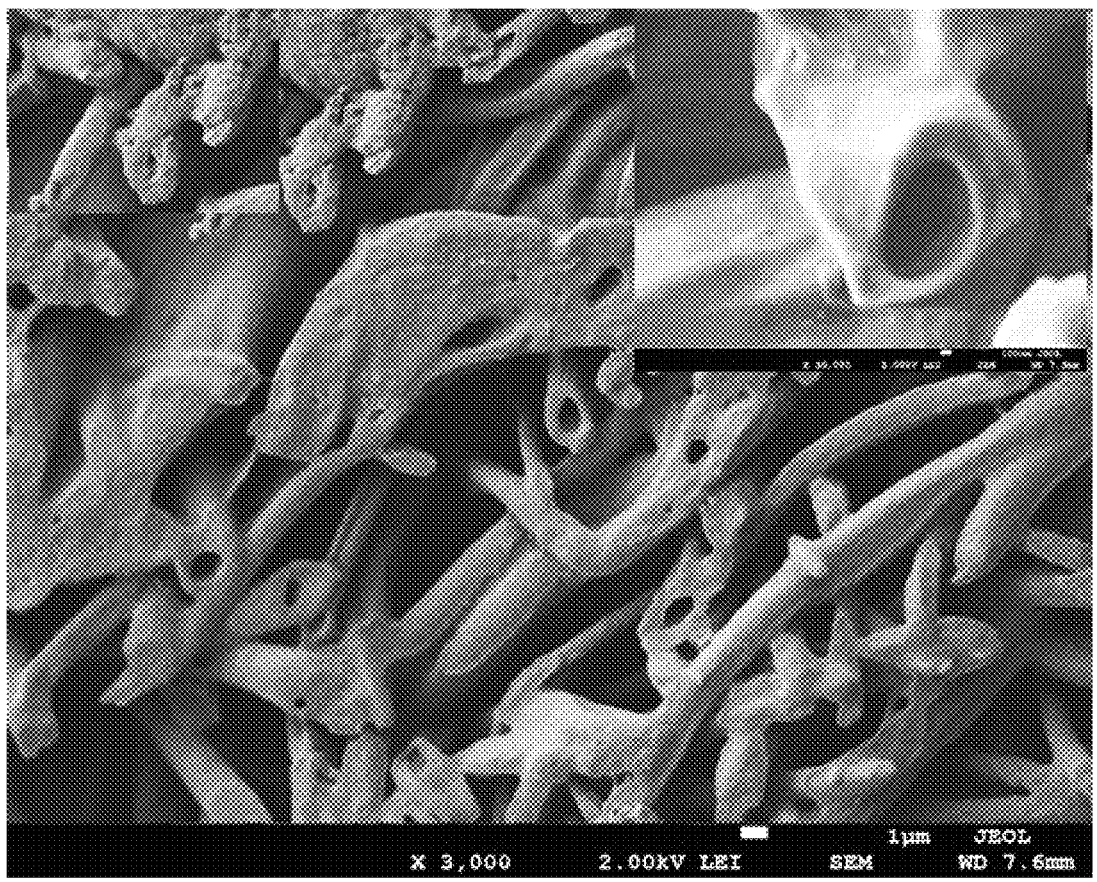
FIGS. 2K-2L. Cross-section by SEM of hollow fibrous scaffolds made of glycerol at a 1 ml/h shell feed rate and at a 0.15 ml/hr core feed rate.

FIG. 1 shows schematic representation of coaxial electrospinning setup for the development of hollow fiber. The setup consisted of two independent syringe pumps which allowed the control of feed rate for the core and shell solutions. The solutions were delivered through single metal needle tip with an 18 gauge outer needle and a 27 gauge inner needle. Furthermore, the inner and outer solutions experience the electrical field simultaneously during the electrospinning process. The glycerol and mineral oil were used as core solution to serve as templates and were removed after electrospinning the fibers.

The process parameters were selected and carried out by initially setting the shell feed rate at 0.5 mL/h and core feed rate at 0.1 mL/h. During the process the formation of the beads occurred in the resultant fibers. The formation of beads happened may be attributed to the shell solution experiencing shear stress from both outer and inner wall resulting in insufficient feed rate for Tailor cone formation. Therefore the feed rate of the shell solution was increased to 1 mL/h to maintain the stable electrospinning process.

Chloroform and acetone (3:1) were selected as solvents for the solid fiber preparation. It was noticed that the needle was blocked by quickly drying shell polymers in less than 15 seconds. The quick drying may be attributed to combined effects of needle configuration in coaxial electrospinning and the solvent system.

Due to different capillary configuration in coaxial electrospinning, the solvent evaporation was slowed down and acetone was replaced with ethanol in the coaxial process to avoid unstable electrospinning conditions. In this stage, the inventors also tried to lower the voltage. However this produced an adverse effect on the fiber morphology.

Subsequently, controlling the feed rate of the core solution was found to be detrimental for successful preparation of hollow fiber using coaxial electrospinning. The initial experiments were carried out by varying the core feed rate with increment of 0.1 from 0.1 mL/h to 0.3 mL/h. Among the different core feed rate, 0.1 mL/h showed acceptable result while higher feed rate caused formation of the beads. The formation of beads implies that the feed rate needs to be controlled more precisely. Based on this the inventors were able to determine advantageous conditions for suitable development of hollow fibers.

The cross-sections of the hollow fibrous scaffolds prepared by using glycerol as a core template are shown by FIG. 2 and demonstrate that 0.05 mL/h of core feed rate is appropriate to develop hollow fiber but the fiber walls were found to be thick.

Increasing the core feed to 0.08 mL/h resulted in larger opening of the hollow and relatively uniform fiber morphology. However, further increasing of the feed rate beyond 0.1 mL/h led to the formation of collapsed fiber and fiber fusion.

This phenomenon may occur during the continuous fiber deposition process. During electrospinning the shell solution quickly dries during deposition. This leads to formation of complete solid phase in the shell of the fiber. However, the evaporation rate of glycerol was very low so it remained in liquid phase in the core throughout the electrospinning process. This might cause tearing of the shell layer and effluence of glycerol to create fiber fusion Therefore, a high core feed rate of glycerol can cause heavy fiber formation with easily deformable liquid phase fiber lumen. The initially deposited shell layer should be mechanically strong enough to bear upper pressure of the layers for continuous fiber deposition to avoid collapse.

Figures 3A, 3B:
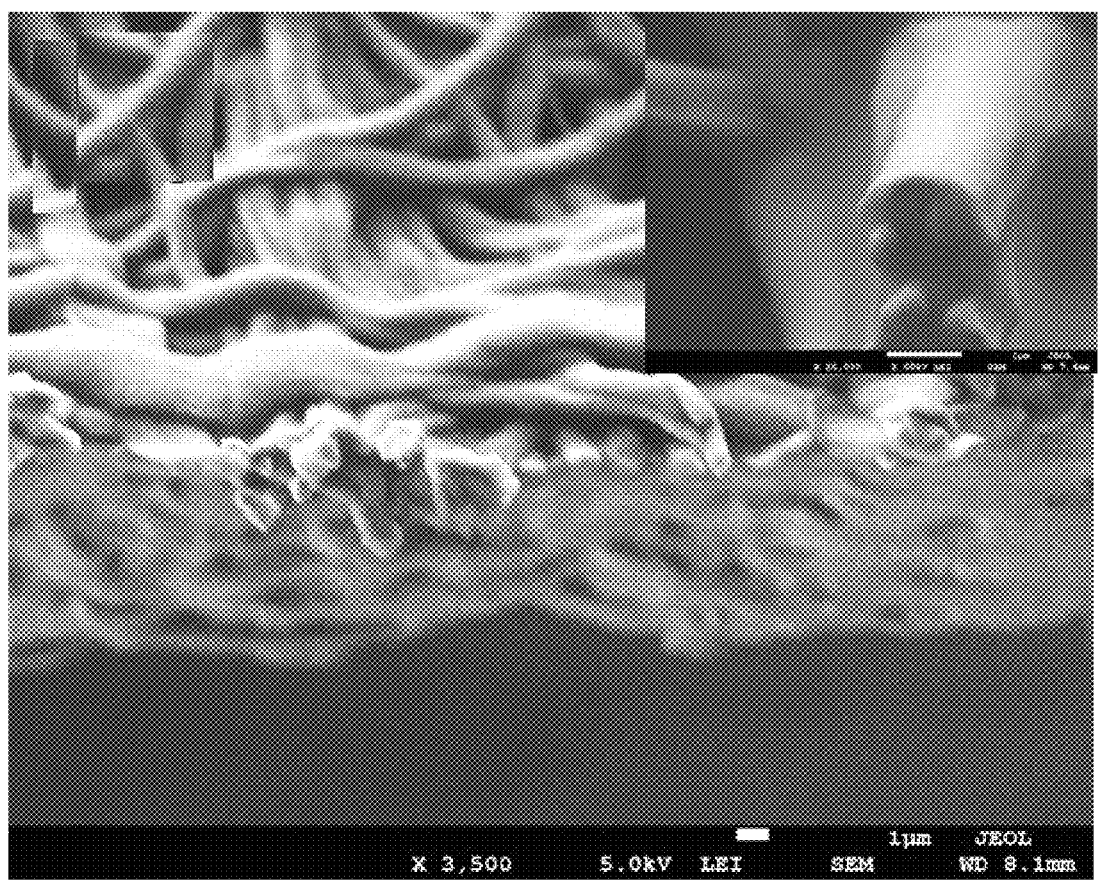
FIGS. 3A-3B. Cross-section by SEM of hollow fibrous scaffolds made of mineral oil at a 1 ml/h shell feed rate and at a 0.08 ml/hr core feed rate.
Figures 3C, 3D:
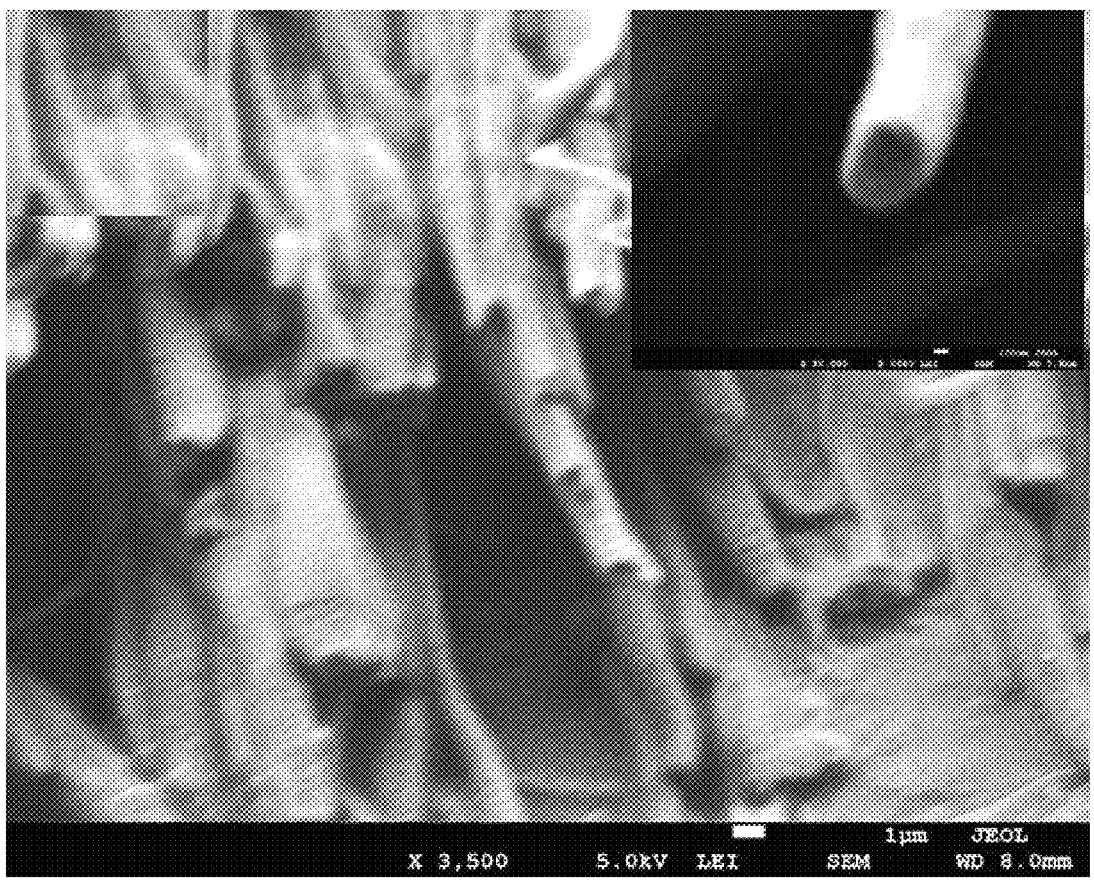
FIGS. 3C-3D. Cross-section by SEM of hollow fibrous scaffolds made of mineral oil at a 1 ml/h shell feed rate and at a 0.10 ml/hr core feed rate.
Figures 3E, 3F:
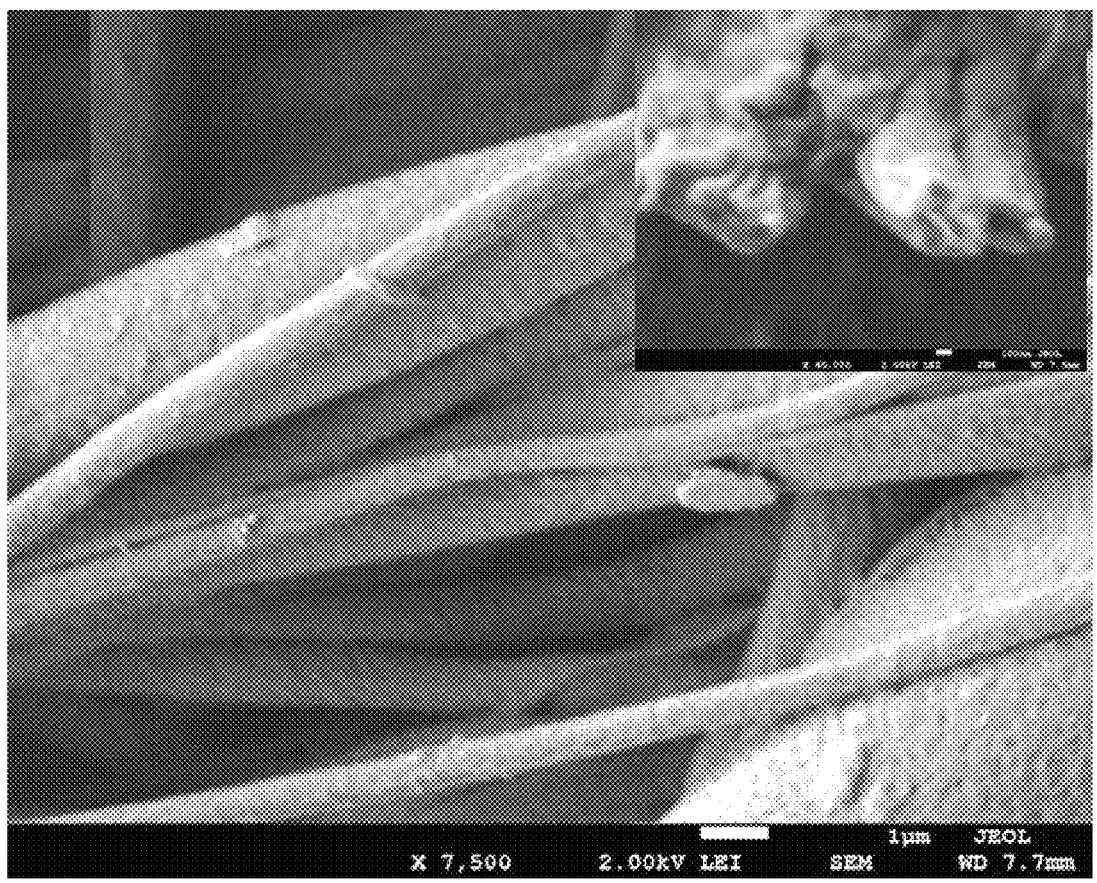
FIGS. 3E-3F. Cross-section by SEM of hollow fibrous scaffolds made of mineral oil at a 1 ml/h shell feed rate and at a 0.12 ml/hr core feed rate.
Figures 4A, 4B:
FIGS. 4A-4D. SEM images of hollow fibrous composite scaffolds: GC (FIG. 4A-4B) and OC (FIG. 4C-4D). See Table 1 for description of GC and OC scaffolds.
Figures 4C, 4D:
Figure 5A:
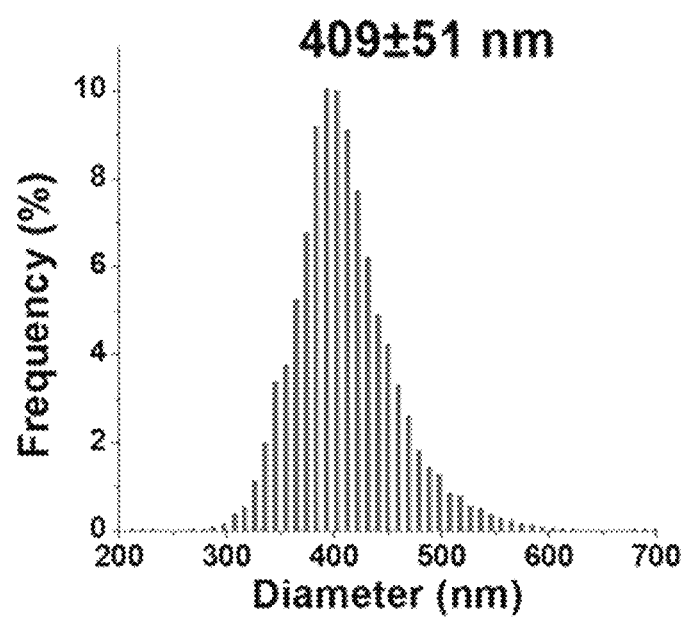
FIGS. 5A-5F illustrate fiber size distributions of the solid scaffolds 50/50 (FIG. 5A) and C4 (FIG. 5B); and the hollow scaffolds GH (FIG. 5C), GC (FIG. 5D), OH (FIG. 5E) and OC (FIG. 5F). See Table 1 for description of 50/50, C4, GH, GC, OH, and OC scaffolds.
Figure 5B:
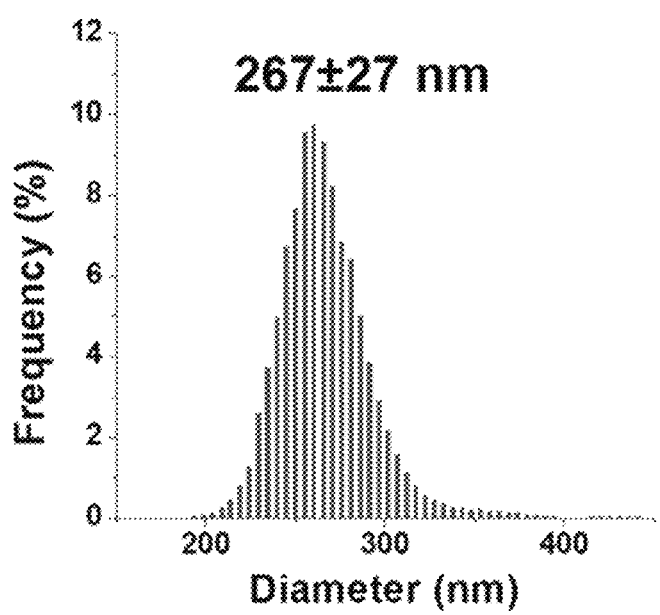
Figure 5C:
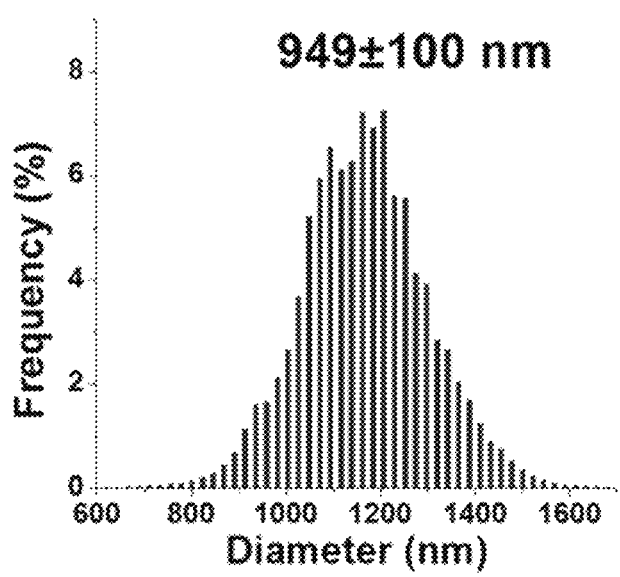
Figure 5D:
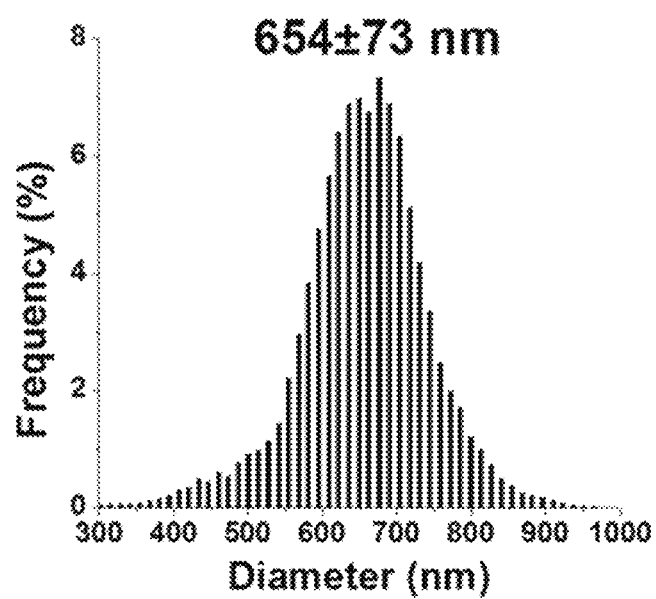
Figure 5E:
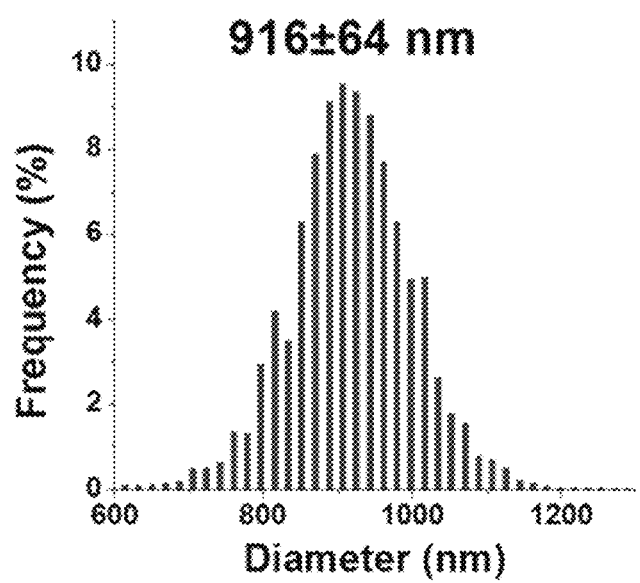
Figure 5F:
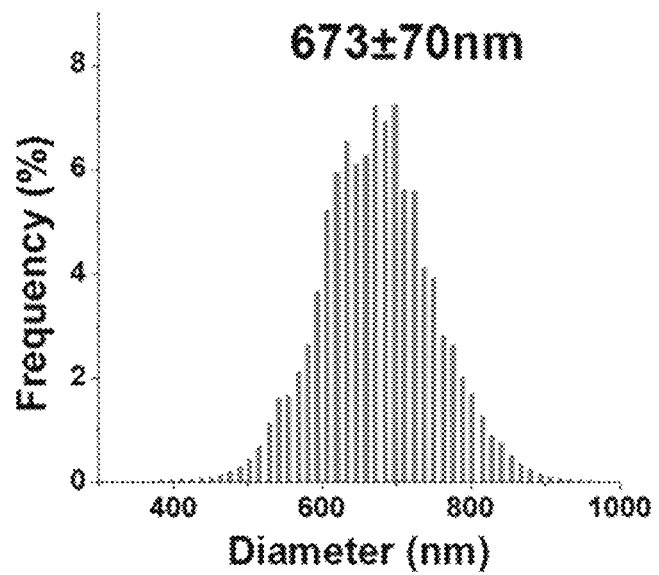
Figure 6A:
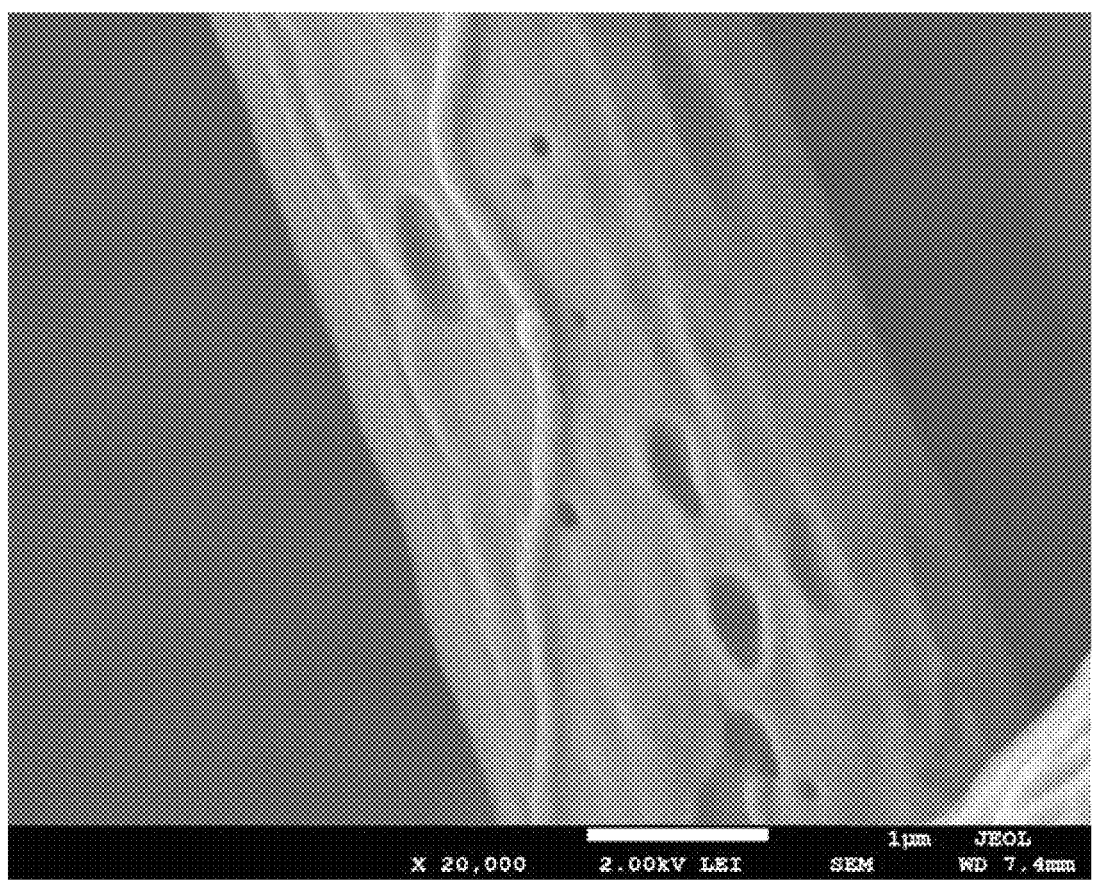
FIGS. 6A-6D illustrate a high resolution SEM images of hollow fibrous scaffolds: GH (FIG. 6A), OH (FIG. 6B), GC (FIG. 6C), and OC (FIG. 6D).
Figure 6B:
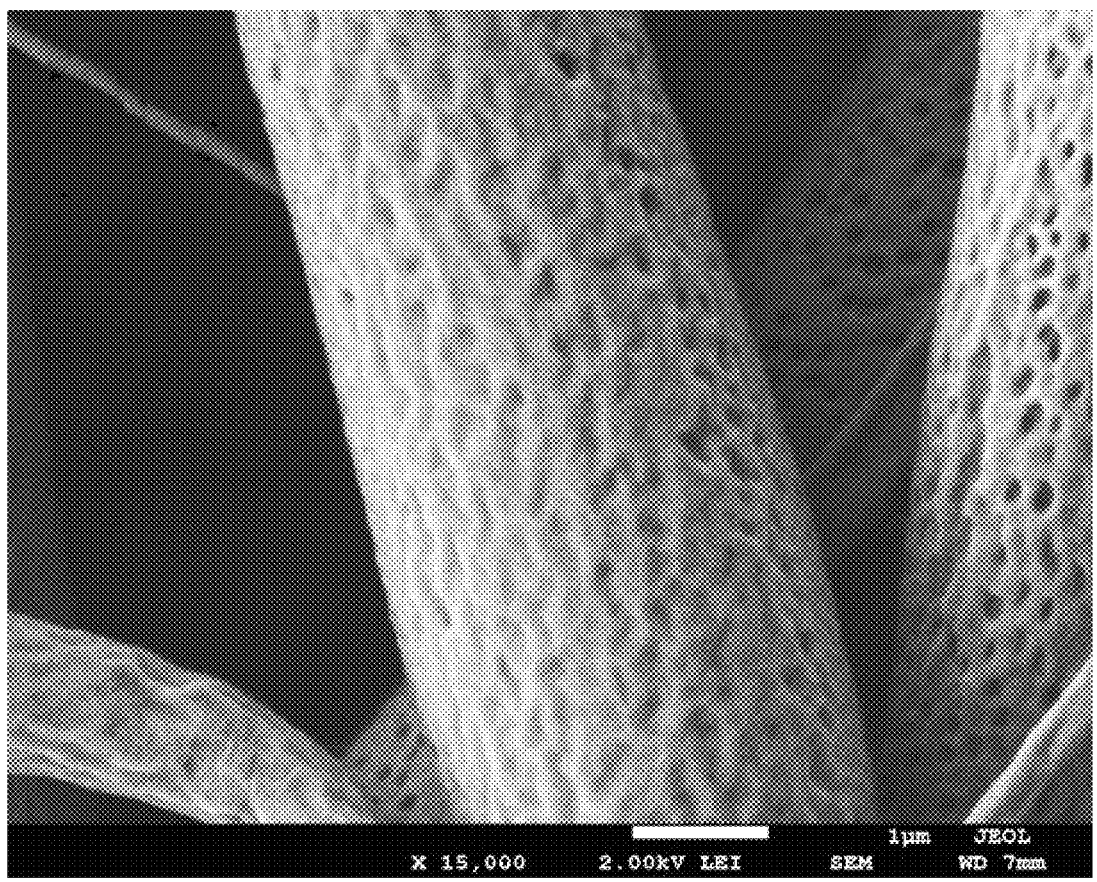
Figure 6C:
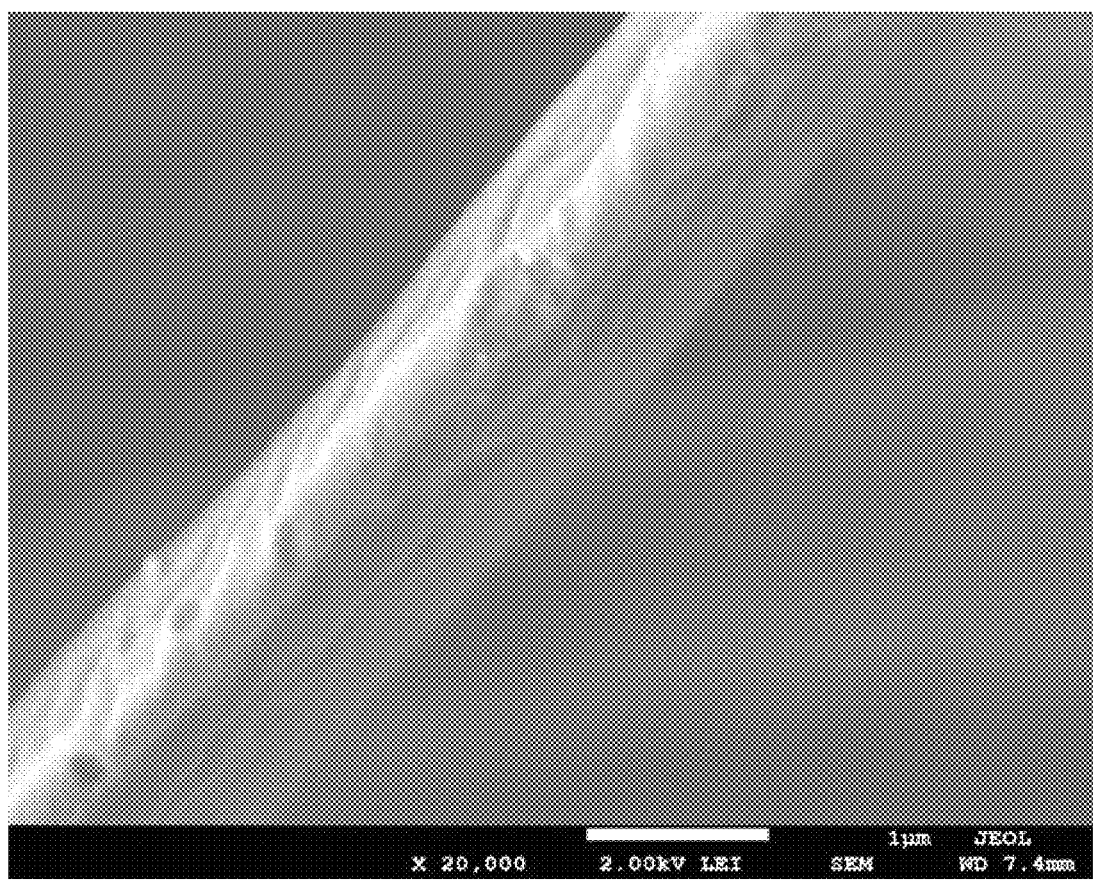
Figure 6D:
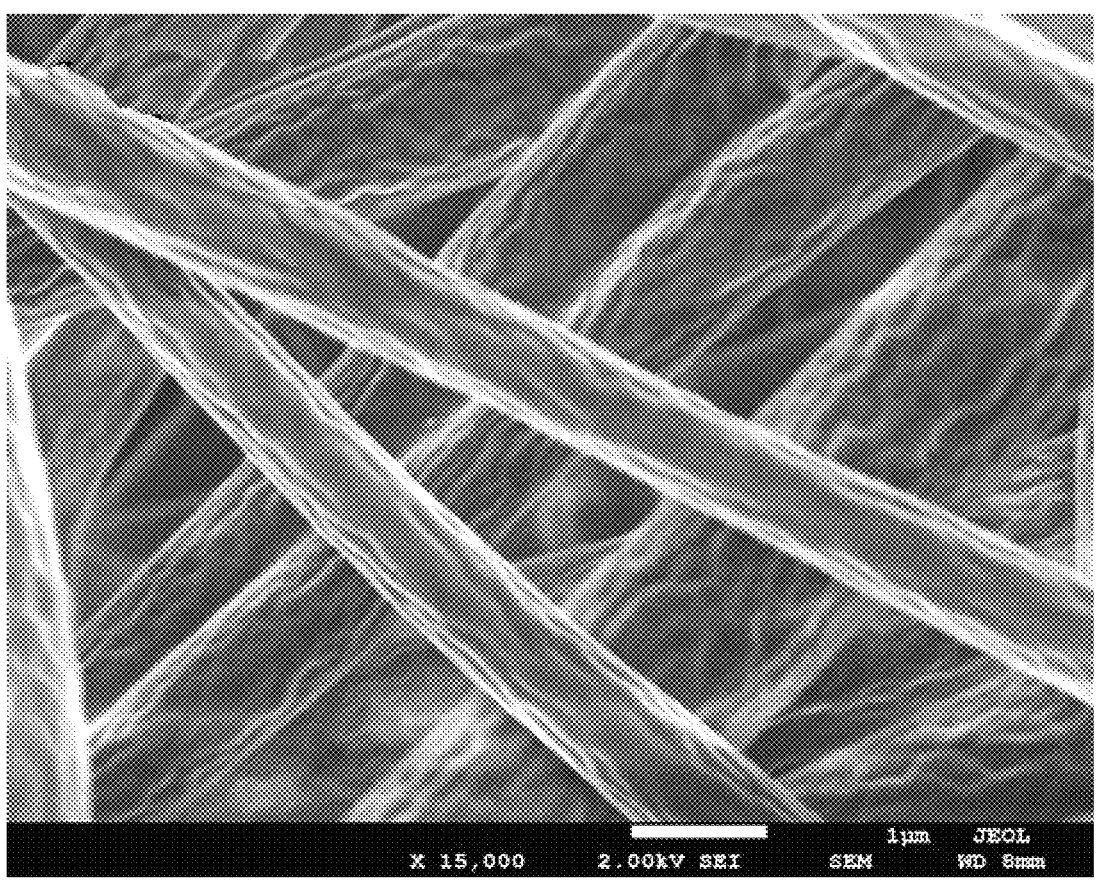
Figure 7A:
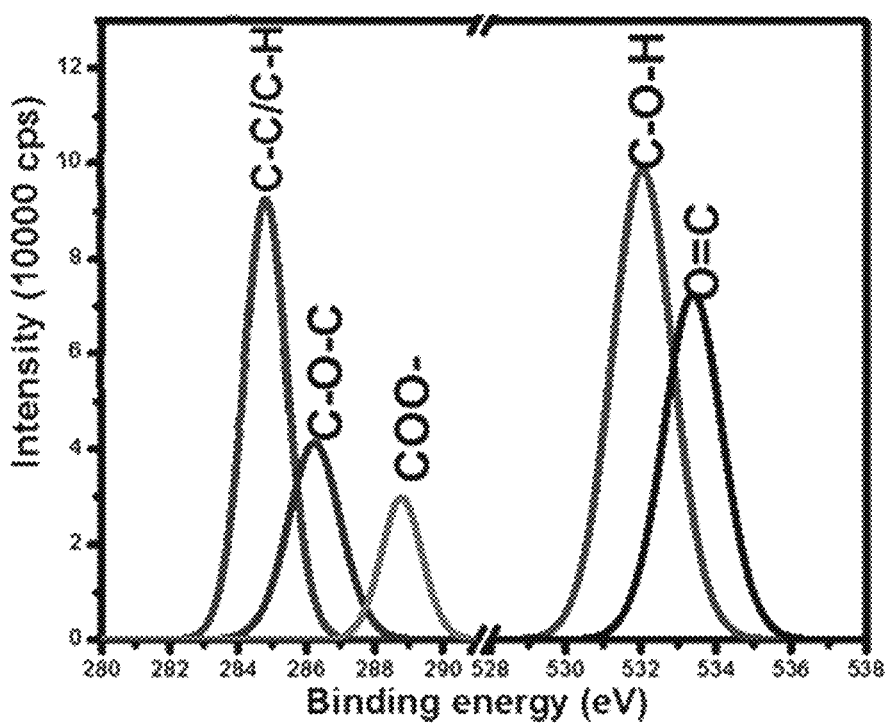
FIGS. 7A-7D. Deconvoluted XPS spectra of hollow fibrous scaffolds: GH (FIG. 7A), OH (FIG. 7B), GC (FIG. 7C), and OC (FIG. 7D).
Figure 7B:
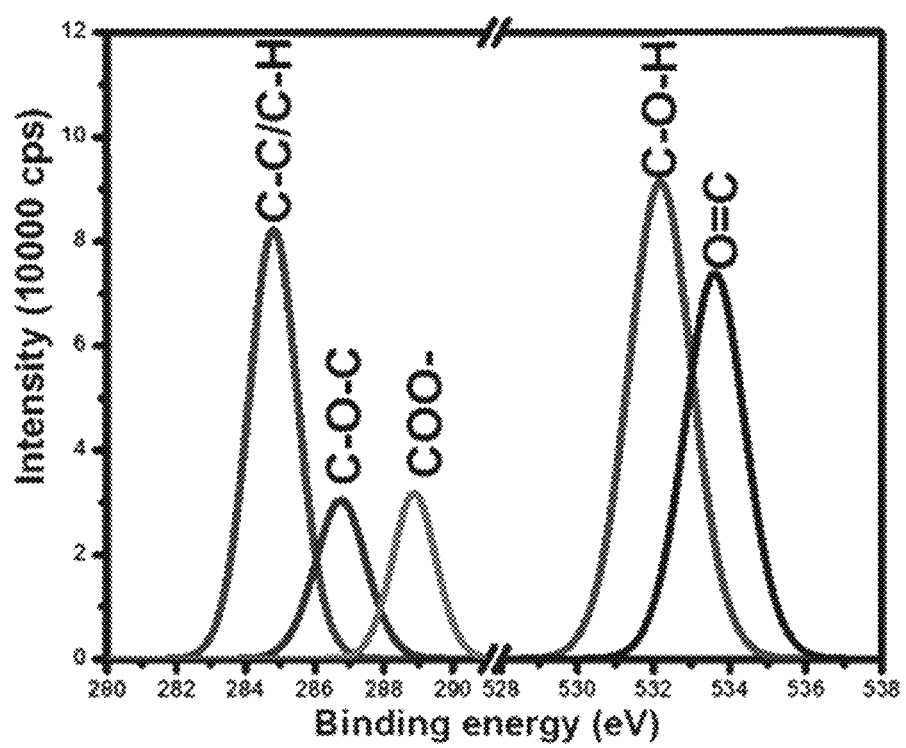
Figure 7C:
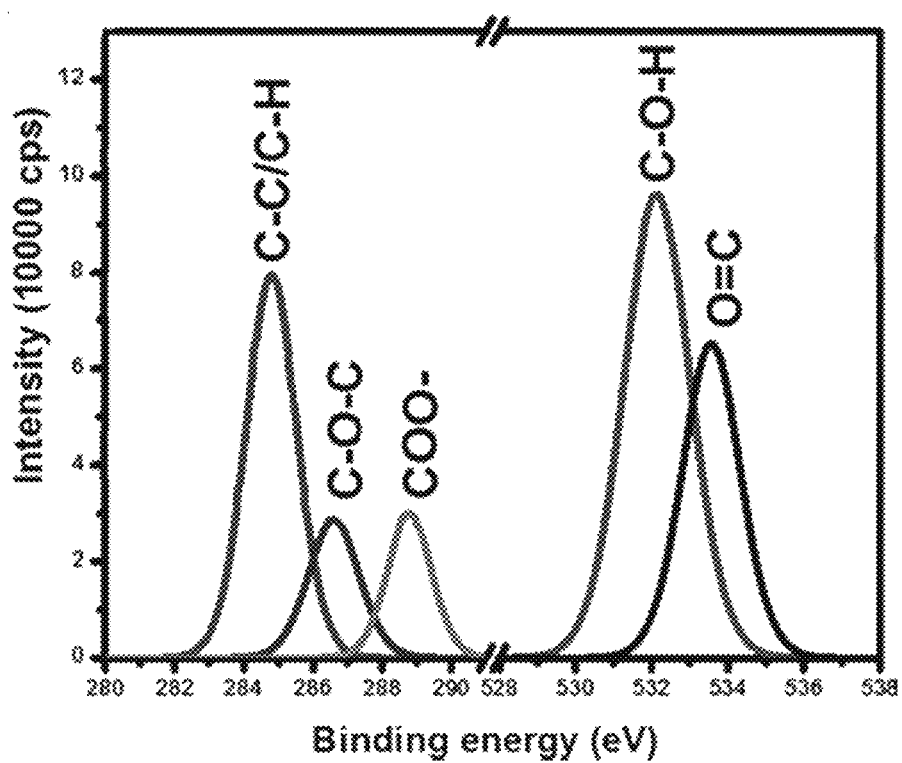
Figure 7D:
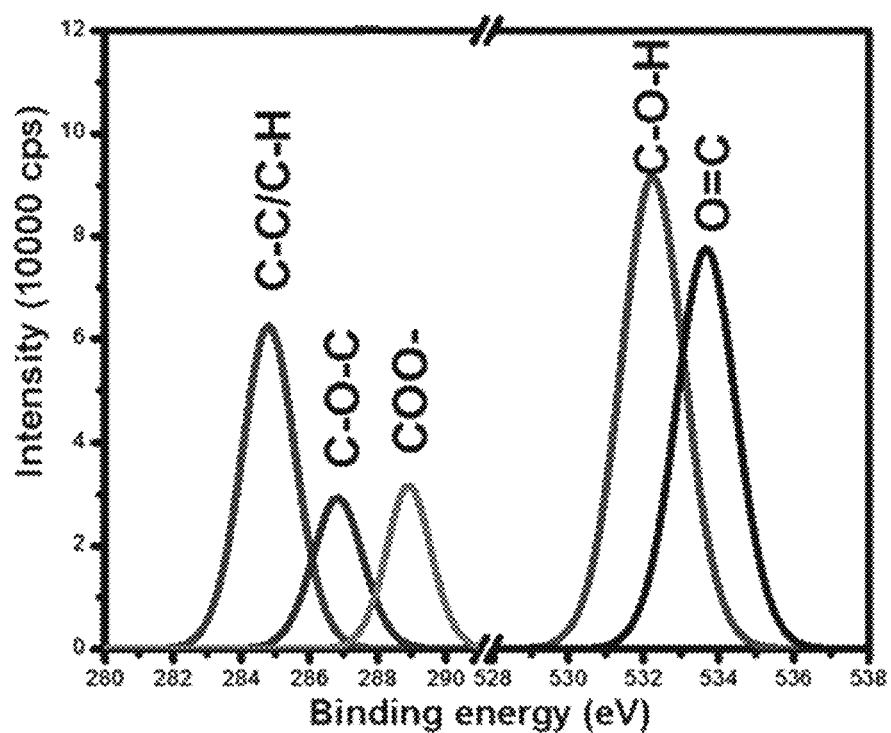

A similar observation was made in the case of mineral oil using a core feed rate of 0.1 mL/h (FIG. 3). The inventors believe that this may be due to the low viscosity of the mineral oil compared to glycerol. Additionally, it was found that the core feed needed to be controlled in a narrower range in order to maintain good fiber morphology without collapsing and fiber fusion. These results show that the feed rate of glycerol at 0.08 mL/h and feed rate of mineral oil at 0.1 mL/h may be selected to prepare hollow composite scaffolds. FIG. 4 shows that these conditions resulted in good hollow fiber morphology.

FIG. 5 shows the fiber size distribution of the hollow and solid fibrous scaffolds. The average fiber size in the scaffolds was found to be twice higher in comparison to PLA/PBS (FIG. 5A) and PLA/PBS/CNF (FIG. 5B) scaffolds of solid fibrous. The difference in sizes may be due to the presence of a core layer during the fiber flight time which creates a resistivity against fiber thinning by the electrical field.

Another potential reason is use of a different configuration of a Tailor cone during the coaxial electrospinning. In the solid fiber fabrication the polymer droplet forms a completely polarized Tailor cone which has influence on the size of the fiber. In case of coaxial electrospinning polarization of the Tailor cone is disturbed by the core solution. Therefore the size of fiber became larger in this case. It should be noted that this phenomena cannot be applied for the coaxial electrospinning in which both core and shell solutions involve spinning. The electric field influences both inner and outer solutions that control the overall fiber morphology and fiber size.

The average diameter of the cores in the hollow fibrous scaffolds was measured using "Digimizer" software from 10 different places of SEM image. Table 2 shows that both core templates had a similar hollow size which was nearly 50% of average fiber size of the scaffolds. However, the core templates showed completely different results on the porosity their fiber walls.

In the case of templates made using a glycerol core only few large pores could be observed and their dispersion was inconsistent as shown in FIG. 6. On the other hand, mineral oil generated uniformly dispersed pores in the fiber wall. This uniform dispersion may be due to the viscosity differences between glycerol and mineral oil. It was noted that both glycerol and mineral oil were slightly soluble with the shell solvent in the presence of ethanol.

The high viscosity of the glycerol produces a stable one directional flow in the electrospinning. However, the less viscous mineral oil generated spray and partly mixed with the ethanol. This spraying and partial mixing encouraged more pore formation on the fiber wall.

Both blended and composite scaffolds were produced having 50 nm pores. The pores in case of blended scaffold are more uniform and spherical as compared to the composite scaffolds. The geometry of the pores could be attributed to the presence of CNF in composite scaffold which preserves its shape and orientation.

TABLE 2

Average diameter of the cores in the hollow fibrous scaffolds

| The scaffold name | Fiber core diameter |
| --- | --- |
| GH (PLA/PBS) | 475 ± 52 nm |
| OH (PLA/PBS) | 485 ± 66 nm |
| GC (PLA/PBS/CNF) | 327 ± 36 nm |
| OC (PLA/PBS/CNF) | 356 ± 47 nm |

FIG. 7 illustrates the XPS spectra of carbon and oxygen in the hollow fibrous scaffolds. The PLA and PBS were formed by the covalent bonding of carbon, hydrogen and oxygen. Among them, hydrogen cannot be detected by XPS because it has no core electrons; see. Stojilovic, N., *Why Can't We See Hydrogen in X-ray Photoelectron Spectroscopy?* Journal of Chemical Education, 2012. 89(10): p. 1331-1332, incorporated herein by reference in its entirety.

Except for hydrogen, each PLA monomer consisted of two C—C—C bonds, one C—C—O bond, one O═C—O bond, one O═C bond and one C—O—C bond. Similar bonds exist in each PBS monomer with double the ratio of the PLA monomer.

The PLA/PBS were homogeneously blended at a 50/50 concentration resulting in a required ideal ratio of 33.33% C—C—C bonds and 16.67% other carbon and oxygen bonds, as shown in Table 2.

From the XPS spectra, two main peaks were observed: the binding energy of the first peak was at 284.79 eV which corresponds to a carbon atom, and the binding energy of another peak was at 532.64 eV which relates to an oxygen atom; see Chastain, J., R. C. King, and J. Moulder, *Handbook of X-ray photoelectron spectroscopy: a reference book of standard spectra for identification and interpretation of XPS data.* 1995: Physical Electronics Eden Prairie, Minn., incorporated herein by reference in its entirety.

As described above in the XPS results, when the PLA/PBS are homogeneously blended with 50/50 concentration, this results in a required ideal ratio of 33.33% C—C—C bonds and 16.67% of other chemical bonds (CCO, COO, OH/COC, —OC). In case of CNF incorporation OH concentration is supposed to be higher due to dominance of OH in the PLA/PBS/CNF composite. The chemical bond composition of each atom was calculated and the results are presented in the Table 2. The bond composition of the scaffold is similar to the ideal bond composition. For example, percentage of C—C—C bond is approximately 35% which is very close to ideal percentage 33.33%. For the PLA/PBS scaffold percentage of other bonds are near to 16.67%. While 25% of OH bond is observed for the PLA/PBS/CNF composite scaffold which highlights dominance of OH in the CNF. Therefore the result implies coherency of the individual material in the composite nanofiber.

TABLE 2

Chemical bond composition and
Binding Energy extracted from XPS peaks

| Name | Binding energy | Concentration (at. %) PLA/PBS | PLA/PBS/CNF |
|---|---|---|---|
| O 1 s | 532.64 | 35.182 | 40.323 |
| C 1 s | 284.79 | 64.818 | 59.677 |
| O 1 s_1_O=C | 532.08 | 18.433 | 15.032 |
| O 1 s_2_C—O—C/OH | 533.48 | 16.749 | 25.291 |
| C 1 s_1_C—C—C | 284.8 | 35.414 | 35.192 |
| C 1 s_2_C—C—O | 286.59 | 15.396 | 12.824 |
| C 1 s_3_O—C=O | 288.82 | 14.008 | 11.662 |

When compared to PLA/PBS blend scaffolds to the PLA/PBS/CNF composite scaffolds containing CNF exhibited higher oxygen concentration.

In case of a PLA/PBS blend, the XPS characteristic of the hollow fibrous scaffolds was found to be similar to that of solid fibrous scaffold. When compared to PLA/PBS blend scaffolds, PLA/PBS/CNF composite scaffolds containing CNF exhibited higher oxygen concentration.

Particularly, the intensity of O—H/O—C bond for the composite scaffolds significantly increased when compared to PLA/PBS scaffolds. The increase in intensity could be due to dominance of OH bonds in the CNF; see Krouit, M., J. Bras, and M. N. Belgacem, *Cellulose surface grafting with polycaprolactone by heterogeneous click-chemistry*. European Polymer Journal, 2008. 44(12): p. 4074-4081, incorporated herein by reference in its entirety.

This result confirms that the materials were homogenously dispersed in the hollow fibrous scaffolds. Whereas overall intensity of the XPS spectra in case of oil templated hollow fibrous scaffolds is lower than the glycerol templated hollow fibrous scaffolds. The lower intensity could be result of high porosity of the fiber wall when oil is used as template.

Figure 8:
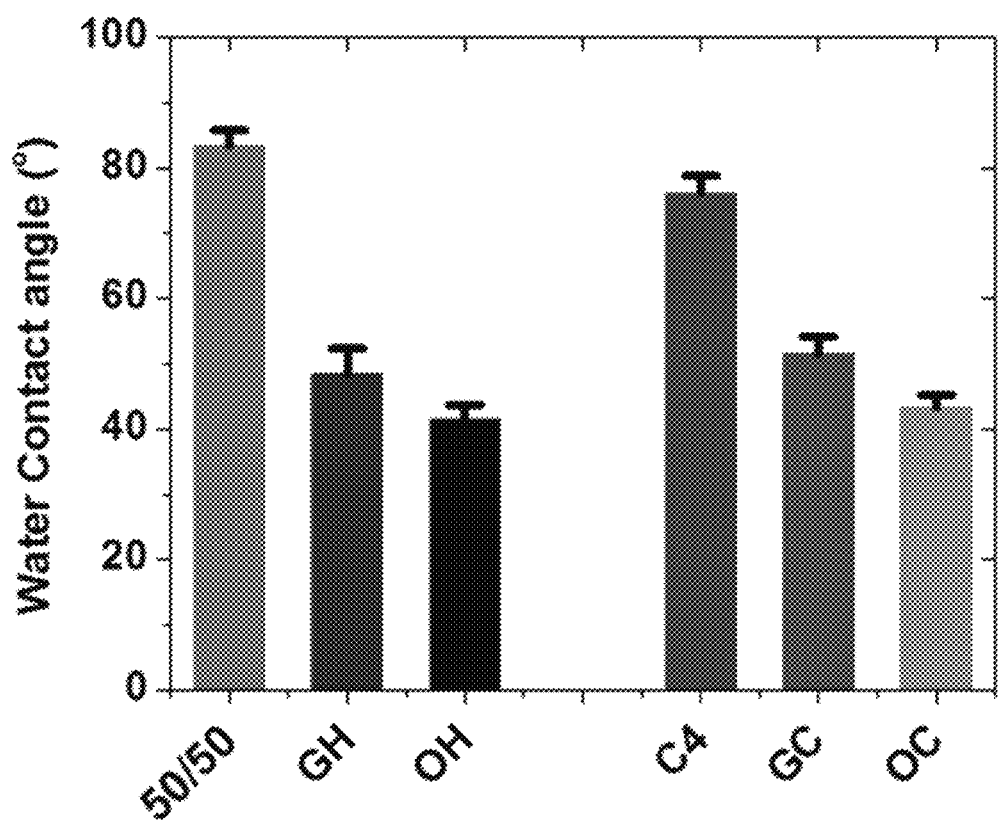
FIG. 8. Water contact angles of hollow fibrous scaffolds (GH, OH, GC, OC) compared to the solid fibrous scaffolds (50/50, C4).

The developed hollow fibrous structure improves the wettability of the scaffold as shown by FIG. 8. For the PLA/PBS blend scaffolds, the water contact angle (WCA) was decreased by ~30° in case of GH and by ~40° in case of OH when compared to solid scaffold.

Similar trends were observed for the composite scaffolds. The WCA of 41.6±2.1° is found in OH scaffold which is the lowest among the hollow fibrous scaffolds. This could be because of uniformly dispersed pores on the fiber wall. This result is favorable because the uniformity in the structure of pores is beneficial for better dispersion of liquids in a scaffold; see Francis, L., et al., *PVDF hollow fiber and nanofiber membranes for fresh water reclamation using membrane distillation*. Journal of Materials Science, 2014. 49(5): p. 2045-2053, incorporated herein by reference in its entirety.

The hydrophilicity of the hollow fibrous scaffolds was found to be much higher than that of solid fibrous scaffolds within 40~80° of WCA; see Arima, Y. et al., *Effect of wettability and surface functional groups on protein adsorption and cell adhesion using well-defined mixed self-assembled monolayers*. Biomaterials, 2007. 28(20): p. 3074-3082; and Wei, J., et al., *Influence of surface wettability on competitive protein adsorption and initial attachment of osteoblasts*. Biomedical Materials, 2009. 4(4): p. 045002, each incorporated herein by reference in their entirety. The improved mobility of liquids enables the interaction of the cells with the scaffolds and enhances the cell adhesion and proliferations.

Moreover as shown by FIG. 9, hollow fibrous structures have an impact on protein adsorption capacity of the scaffolds. The mineral oil templated hollow fibrous scaffolds showed double protein adsorption capacity when compared to solid fibrous scaffolds. The enhanced adsorption capacity may be due to the increased surface area because of hollow conduits and micropore formation on the fiber wall. Also, higher hydrophilicity increases the protein adsorption capacity of the scaffolds.

FIG. 10 depicts GFP/DAPI staining images of the hollow fibrous scaffolds after 7 days. All scaffolds supported better adhesion and dispersion of the cells through entire area. The mineral oil templated hollow scaffolds showed more occupied cell attachment compared to the glycerol templated hollow scaffolds.

In the case of GH and GC scaffolds, produced using a glycerol core, a number of black spots can be observed from the staining image which implies that no cell attachment occurred in those areas.

Meanwhile, OH and OC scaffolds, produced using a mineral oil core, showed completely overlapped cell attachment without any black spots. This could be strongly correlated with overlarge surface area of the microporous hollow fibrous scaffolds. The enhanced surface energy and enriched protein adsorption capacity of the scaffold are the contributing factors for the better cell adhesion performance of OH and OC scaffolds; Arima et al., Electrospun 1,6-diisocyanatohexane-extended poly(1,4-butylene succinate) fiber mats and their potential for use as bone scaffolds. Polymer, 2009. 50(6): p. 1548-1558; Garcia-Orue, I., et al., Chapter 2—Nanotechnology approaches for skin wound regeneration using drug-delivery systems A2—*Grumezescu, Alexandru Mihai*, in Nanobiomaterials in Soft Tissue Engineering. 2016, William Andrew Publishing. p. 31-55; and Tallawi, M., et al. *Poly (glycerol sebacate)Poly (butylene succinate-dilinoleate) Blends as Candidate Materials for Cardiac Tissue Engineering*. in Macromolecular Symposia. 2013. Wiley Online Library, each incorporated herein by reference in their entirety.

Figure 11A:
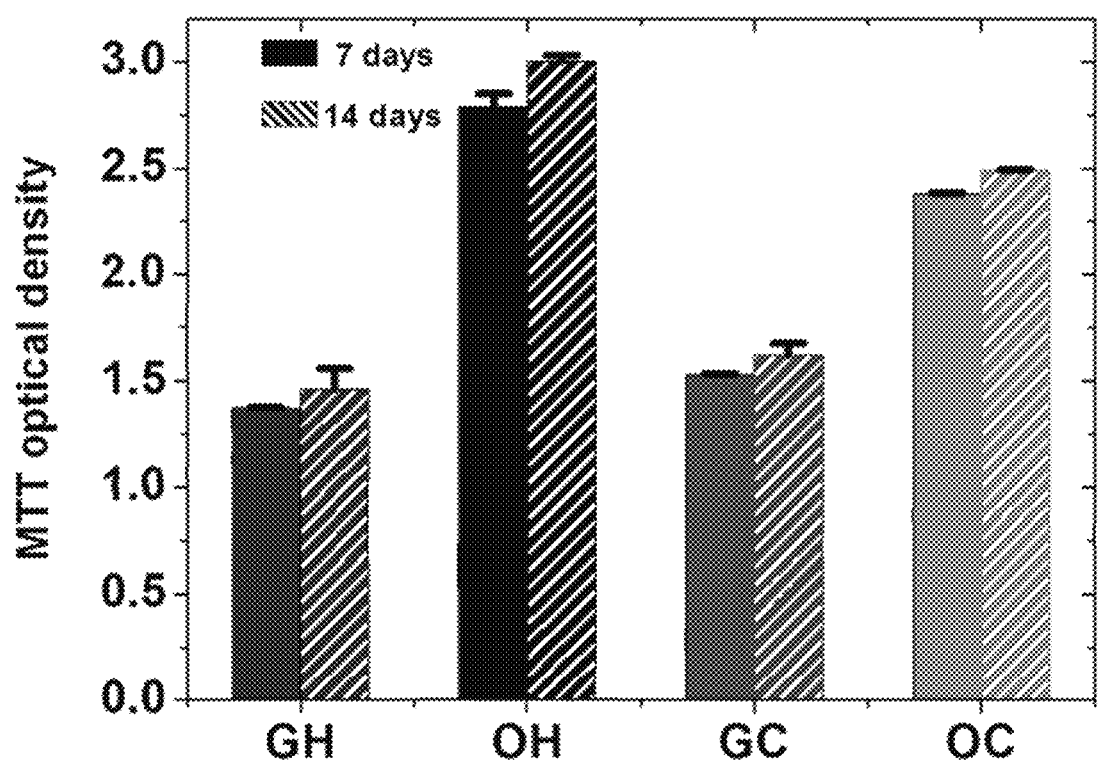
FIG. 11A. MTT optical density value for the hollow fibrous scaffold after one and two weeks of cell culturing.
Figure 11B:
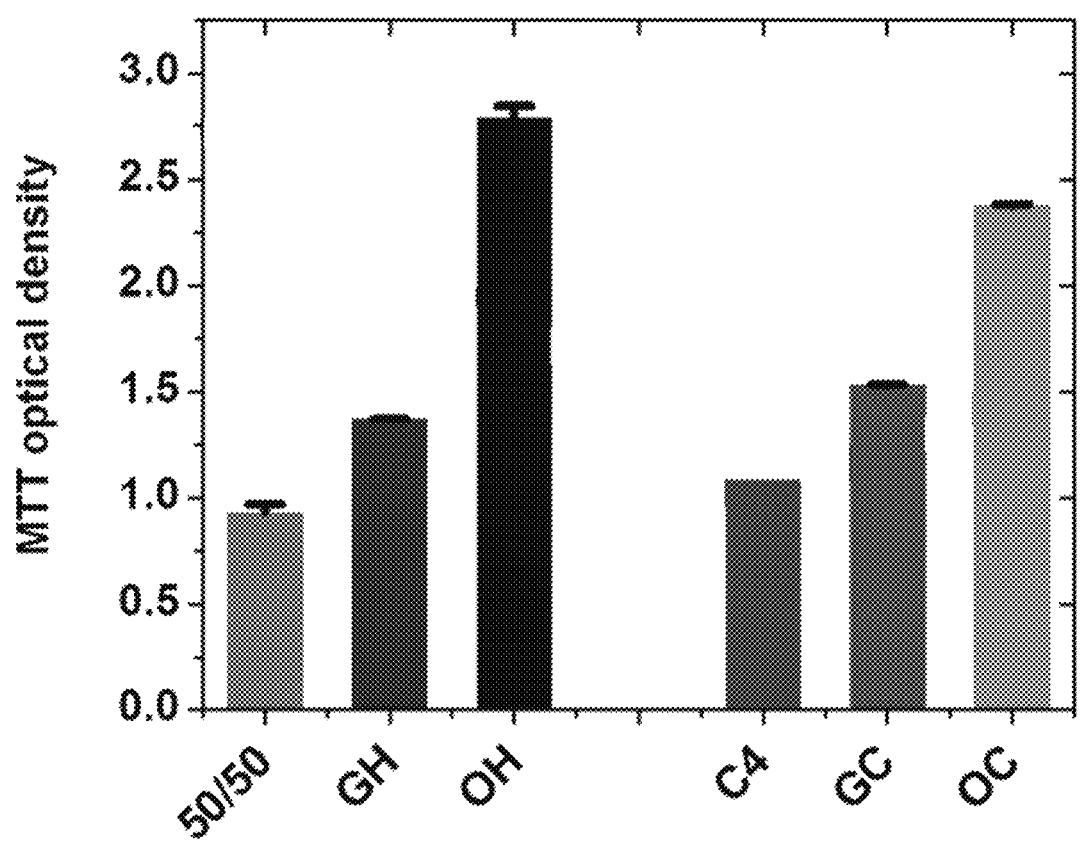
FIG. 11B. Viability comparison after one week between solid and hollow fibrous scaffolds.

The cell proliferation result for the hollow fibrous scaffolds at 7 and 14 days by MTT assay can be observed in FIG. 11A. Similarly, in the solid fibrous scaffolds the rapid increase in cell proliferation was achieved in the first week and followed by a slower increase in the second week. Whereas, the hollow fibrous scaffolds showed a higher cell proliferation rate compared to the solid fibrous scaffolds (FIG. 11B). The highest cell proliferation rate is found in case of OH scaffold which is even higher than that of OC scaffolds. The improved proliferation rate shows the importance of uniform pore formation on the fiber wall. The microporous hollow fibrous scaffolds can provide for better transport of nutrients, oxygen and other important biomolecules to the cells. The cells with the help of newly developed scaffold can be provided with an advantageous microenvironment for the growth, propagation and viability.

As demonstrated herein, homogenously blended microporous hollow fibrous scaffolds were successfully synthesized from PLA/PBS blends and CNF reinforced composites using mineral oil as a core template. Among the coaxial electrospinning parameters core and shell feed rate were found to be the most determining parameters to generate uniform hollow fiber without fusion and beads. The mineral oil and glycerol both as core templates allowed hollow fiber formation form PLA/PBS blends and CNF reinforced composites in electrospinning. The mineral oil resulted in formation of uniformly dispersed microspores on the fiber wall. Also, the surface composition of the hollow fibrous scaffolds was not influenced by the core templates. The high porosity in the fiber wall was confirmed for the oil templated hollow fibrous scaffolds. The surface properties such as wettability and protein adsorption capacity were remarkably improved in the presence of microporous and hollow fibrous structure. Finally, the microporous hollow fibrous scaffolds showed enhanced cell adhesion and proliferation performance than the solid fibrous scaffolds.

The invention claimed is:

1. A method for repairing living tissue, comprising
   applying a hollow fiber scaffold on, in or around living tissue in need of repair,
   wherein the hollow fibers of the hollow fiber scaffold fibers have a hollow core and a peripheral shell,
   wherein the peripheral shell comprises a mixture of homogenously dispersed polylactic acid (PLA), polybutylene succinate (PBS) and cellulose nanofibers (CNF);
   wherein the hollow fibers have an average diameter ranging from 400 to 1,000 nm and the hollow core has an average diameter ranging from 300 to 900 nm.
2. The method of claim 1, wherein the living tissue in need of repair is a vascular tissue.
3. The method of claim 1, wherein the living tissue in need of repair is an epithelial tissue.
4. The method of claim 1, wherein the peripheral shell has pores ranging in size from 25 to 100 nm in diameter.
5. The method of claim 1, wherein the peripheral shell has pores ranging in size from 40 to 60 nm in diameter.
6. The method of claim 1, wherein the peripheral shell has uniformly distributed pores wherein an average size or numbers of pores in different areas of the peripheral shell varies by no more than 10%.
7. The method of claim 1, wherein the hollow fiber scaffold has an interconnected macroporous structure.
8. The method of claim 1, wherein the peripheral shell comprises micropores; and wherein the hollow core and the micropores of the peripheral shell provide enhanced diffusion of nutrients and oxygen to the cells grown on or with the scaffold as compared to cells grown on scaffold comprising solid fibers.
9. The method of claim 1, wherein the hollow fiber scaffold is a portion of a sterile or aseptic patch, packing, dressing or bandage applied to the tissue in need of repair, and wherein the hollow fiber scaffold comprises cells or one or more biologically active agents.

* * * * *